(12) United States Patent
Xiang et al.

(10) Patent No.: US 10,373,708 B2
(45) Date of Patent: Aug. 6, 2019

(54) SYSTEMS AND METHODS FOR GENERATING BIOMARKER SIGNATURES WITH INTEGRATED DUAL ENSEMBLE AND GENERALIZED SIMULATED ANNEALING TECHNIQUES

(71) Applicant: Philip Morris Products S.A., Neuchatel (CH)

(72) Inventors: Yang Xiang, Neuchatel (CH); Julia Hoeng, Corcelles (CH); Florian Martin, Peseux (CH)

(73) Assignee: Philip Morris Products S.A., Neuchatel (CH)

( * ) Notice: Subject to any disclaimer, the term of this patent is extended or adjusted under 35 U.S.C. 154(b) by 280 days.

(21) Appl. No.: 14/409,679

(22) PCT Filed: Jun. 21, 2013

(86) PCT No.: PCT/EP2013/062982
§ 371 (c)(1),
(2) Date: Dec. 19, 2014

(87) PCT Pub. No.: WO2013/190085
PCT Pub. Date: Dec. 27, 2013

(65) Prior Publication Data
US 2015/0154353 A1    Jun. 4, 2015

Related U.S. Application Data

(60) Provisional application No. 61/662,812, filed on Jun. 21, 2012.

(51) Int. Cl.
*G06N 20/00* (2019.01)
*G06N 5/02* (2006.01)
*G16B 40/00* (2019.01)

(52) U.S. Cl.
CPC ............. *G16B 40/00* (2019.02); *G06N 5/027* (2013.01); *G06N 20/00* (2019.01)

(58) Field of Classification Search
CPC ........ G06F 19/24; G06N 5/02; G06N 99/005; G06N 20/00
See application file for complete search history.

(56) References Cited

U.S. PATENT DOCUMENTS

| | | | |
|---|---|---|---|
| 2003/0130798 A1 | 7/2003 | Hood et al. | |
| 2005/0086035 A1 | 4/2005 | Peccoud et al. | |

(Continued)

FOREIGN PATENT DOCUMENTS

| | | |
|---|---|---|
| JP | 2005-538437 A | 12/2005 |
| JP | 2008-090833 A | 4/2008 |

(Continued)

OTHER PUBLICATIONS

Glez-Peña, D., et al. "A simulated annealing-based algorithm for iterative class discovery using fuzzy logic for informative gene selection." Journal of Integrated OMICS 1.1 (2010): 66-77.*

(Continued)

*Primary Examiner* — Eric Nilsson
(74) *Attorney, Agent, or Firm* — Sterne, Kessler Goldstein & Fox P.L.L.C.

(57) ABSTRACT

Described herein are systems and methods for classifying a data set using an ensemble classification technique. Classifiers are iteratively generated by applying machine learning techniques to a training data set, and training class sets are generated by classifying the elements in the training data set according to the classifiers. Objective values are computed based on the training class sets, and objective values associated with different classifiers are compared until a desired number of iterations is reached, and a final training class set is output.

20 Claims, 10 Drawing Sheets

(56) References Cited

U.S. PATENT DOCUMENTS

| | | |
|---|---|---|
| 2005/0273305 A1 | 12/2005 | Thalhammer-Reyero |
| 2006/0047616 A1 | 3/2006 | Cheng et al. |
| 2006/0074824 A1 | 4/2006 | Li |
| 2006/0074826 A1 | 4/2006 | Heumann et al. |
| 2006/0177827 A1 | 8/2006 | Dejori et al. |
| 2007/0198653 A1 | 8/2007 | Jarnagin et al. |
| 2009/0326897 A1 | 12/2009 | Schuppert et al. |
| 2010/0216660 A1 | 8/2010 | Nikolsky et al. |
| 2012/0054184 A1 | 3/2012 | Masud |
| 2012/0143805 A1 | 6/2012 | Gold et al. |
| 2013/0024177 A1 | 1/2013 | Nolan |
| 2013/0262465 A1 | 10/2013 | Galle |
| 2014/0214336 A1 | 7/2014 | Martin et al. |
| 2015/0178639 A1 | 6/2015 | Martin et al. |
| 2015/0220838 A1 | 8/2015 | Martin et al. |

FOREIGN PATENT DOCUMENTS

| | | |
|---|---|---|
| JP | 2009-282686 A | 12/2009 |
| WO | WO 2005052181 | 6/2005 |
| WO | WO-2011005893 A2 | 1/2011 |
| WO | WO 2013034300 | 3/2013 |
| WO | WO 2013190083 | 12/2013 |
| WO | WO 2013190084 | 12/2013 |
| WO | WO 2013190085 | 12/2013 |

OTHER PUBLICATIONS

Dietterich, T. "Ensemble methods in machine learning." International workshop on multiple classifier systems. Springer Berlin Heidelberg, 2000.*

Huang, N., et al. "Characterising and predicting haploinsufficiency in the human genome." PLoS Genet 6.10 (2010): e1001154.*

Yang, P., et al. "A review of ensemble methods in bioinformatics." Current Bioinformatics 5.4 (2010): 296-308.*

"A simulated annealing-based algorithm for iterative class discovery using fuzzy logic for informative gene selection", Glez-Pena, Daniel, et al., Journal of Integrated Omics, vol. 1, No. 1, Feb. 1, 2011.

"Optimization by simulated annealing", Kirkpatrick, S., et al., Science, American Association for the Advancement of Science, Washington, D.C., vol. 22, No. 4958, May 13, 1983, pp. 671-680.

"Combining labeled and unlabeled data with co-training", Blum, A., et a., Proceedings of the 11th Annual Conference on Computational Learning Theory. Colt '98, Madison, WI, Jul. 24-26, 1998 (Annual Conference on Computational Learning Theory), New York, NY, pp. 92-100.

"Parmeter determination of support vector machine and feature selection using simulated annealing approach", Lin, Shih-Wei, et al., Applied Soft Computing, Vo. 8, No. 4, Sep. 1, 2008, pp. 1568-4946.

"A Review of Ensemble Methods in Bioinformatics", Pengyi, Yang, et al., Current Bioinformatics, vol. 5, No. 4, Dec. 1, 2010 pp. 296-308.

"Iterative Ensemble Classification for Relational Data: A Case Study of Semantic Web Services", Andreas, Heb, et al., ECML 2004, LNAI 3201, Jan. 1, 2004, pp. 156-167, retrieved from the Internet: URL:http://citeseerx.ist.psu.edu/viewdoc/download?doi=10.1.1.3.658&rep=rep1&type=pdf (retrieved on Oct. 22, 2013).

International Search Report and Written Opinion dated Nov. 13, 2013 in International Application No. PCT/EP2013/062982.

Bhattacharjee et al., "Bayesian integrated functional analysis of microarray data" Bioinformatics, 20:2943-2953 (2004).

Chung, "Chapter 1: Eigenvalues and the laplacian of a graph," Spectral Graph Theory, American Mathematical Society, Providence, pp. 1-22 (1997).

Haggerty et al., "Chemical genomic profilling of biological networks using graph theory and combinations of small molecule perrturbations," J Am Chem Soc., 125:10543-10545 (2003).

Hoeng et al., "A network-based approach to quantifying the impact of biologically active substances", Drug Discovery Today, 17: 413-418 (2012).

International Search Report and Written Opinion dated Nov. 27, 2013 in International Application No. PCT/EP2013/062980.

International Search Report dated Jul. 25, 2013 and Written Opinion dated Mar. 12, 2014 in International Application No. PCT/EP2012/003760.

International Search Report dated Oct. 11, 2013 and Written Opinion dated Dec. 23, 2014 in International Application No. PCT/EP2013/062979.

Lee et al., "Analysis of AML genes in dysregularted molecular networks," BMC Bioinformatics, 10:S2 (2009).

Lim et al., "Master regulartors used as breast cancer metastasis classifier", Pac symp Biocomput., Jan. 1, 2009, pp. 504-515, retrieved from the Internet: URL:http://www.ncbi.mlm.nih.gov/pmc/articles/PMC2740937/pdf/nihms106219.pdf (retrieved on Sep. 12, 2013).

Martin et al., "Assessment of network perturbation amplitudes by applying high-throughput data to causal biological networks", BMC Systems Biology, Biomed Central Ltd, 6:54-71 (2012).

Michiels et al., "Prediction of cancer outcome with microarrays: a multiple random validation strategy", The Lancet, Lancet Limited, London GB, 365:488-492 (2005).

Paul et al., "The stability of feature selection and class prediction from ensemble tree classifiers", Proceedings of the European Symposium on Artifical Neural Networks, Computational Intellignce and Machine Learning 2012, Apr. 27, 2012 pp. 263-268.

Saigo, "Mean—Adjusted bootstrap for two—Phase Samplling", Survey Methodology, Jun. 1, 2007, retrieved from the Internet: URL:http://www.statcan.gc.ca/ads-annonces/12-001-x/9853-eng.pdf (retrieved on Oct. 29, 2013).

Selventa—"Reverse Causal Reasoning Methods—White Paper", Anonymous, Retrieved from the Internet: URL:http://www.selventa.com/attachments/white_papers/reverse-causal-reasoning.pdf (retrieved on Aug. 17, 2012).

Tegner et al., "Perturbation to uncover gene networks," Trends in Genetics, 23:34-41 (2006).

Tibshirani et al., "Diagnosis of multiple cancer types by shrunken centroids of gene expression", PNAS USA, 99:6567-6572 (2002).

Weston et al., "Feature selection for SVM's", Advances in Neural Information Processing Systems 13, pp. 668-674, retrieved from the Internet: URL:http://www0.cs.ucl.ac.uk/staff/M. Pontil/reading/featsel.pdf (retrieved on Jun. 13, 2013).

Westra et al., "Construction of a computable cell proliferation network focused on non-diseased lung cells", MBC Systems Biology, 5:105 (2011) (16 pages).

Yamanishi et al., "Extraction of correlated gene clusters from multiple genomic data by generalized kernel cannical correlation analysis," Bioinformatcs, 19:i323-i330 (2003).

Burgoon et al., "Automated quantitative dose-response modeling and point of departure determination for large toxicogenomic and high-throughput screening data sets," Toxicol Sci., 104:412-418 (2008).

Ekins et al., "Techniques: application of systems biology to absorption, distribution, metabolism, excretion and toxic," Trends Pharmacol Sci., 26:202-209 (2005).

Marchal et al., Computational Biology and Toxicogenomics, Chapter 3 of Predictive Toxicology (ed. Helma, C.) 37-92 (2005).

Kim et al., "Can markov chain models mimix biological regulation?" Journal of Biological System, 10:337-357 (2002).

Nie et al., "Predictive toxicogenomics approaches reveal underlying molecular mechanisms of nongenotoxic carcinogenicity," Mol Carcinog., 45:914-933 (2006).

Toyoshiba et al., "Gene interaction network suggests dioxin induces a significant linkage between aryl hydrocarbon receptor and retinoic acid receptor beta," Environ Health Perspect., 112:1217-1224 (2004).

U.S. Appl. No. 14/342,689 Non-Final Office Action dated Apr. 22, 2016.

Liu, Kunhong, "Applications of multiple classifier ensemble system in gene microarray data analysis," China doctoral Thesis Full-Text Database Information Technologu Series, 2009(6): 1140-10 (2009) (Chinese language).

(56) References Cited

OTHER PUBLICATIONS

Nasierding, G., et al. "Dual-Random Ensemble Method for Multi-Label Classification of Biological Data," Proceedings of the 2009 International Symposium on Bioelectronics and Bioinformatics. Melbourne, Australia, 2009, pp. 49-52.

Vinzamuri, B., et al. "Designing an Ensemble Classifier over Subspace Classifiers using Iterative Convergence Routine," Proceedings of the 20th ACM Conference on Information and Knowledge Management, CIKM 2011, Glasgow, United Kingdom, 2011, pp. 693-698.

* cited by examiner

SYSTEMS AND METHODS FOR GENERATING BIOMARKER SIGNATURES WITH INTEGRATED DUAL ENSEMBLE AND GENERALIZED SIMULATED ANNEALING TECHNIQUES

CROSS REFERENCE TO RELATED APPLICATIONS

This application is a U.S. Nationalization of PCT Application No. PCT/EP2013/062982 filed Jun. 21, 2013, which claims the benefit of U.S. Provisional Application No. 61/662,812, filed Jun. 21, 2012, the entireties of which are incorporated herein by reference.

BACKGROUND

In the biomedical field it is important to identify substances that are indicative of a specific biological state, namely biomarkers. As new technologies of genomics and proteomics emerge, biomarkers are becoming more and more important in biological discovery, drug development and health care. Biomarkers are not only useful for diagnosis and prognosis of many diseases, but also for understanding the basis for development of therapeutics. Successful and effective identification of biomarkers can accelerate the new drug development process. With the combination of therapeutics with diagnostics and prognosis, biomarker identification will also enhance the quality of current medical treatments, thus play an important role in the use of pharmacogenetics, pharmacogenomics and pharmacoproteomics.

Genomic and proteomic analysis, including high throughput screening, supplies a wealth of information regarding the numbers and forms of proteins expressed in a cell and provides the potential to identify for each cell, a profile of expressed proteins characteristic of a particular cell state. In certain cases, this cell state may be characteristic of an abnormal physiological response associated with a disease. Consequently, identifying and comparing a cell state from a patient with a disease to that of a corresponding cell from a normal patient can provide opportunities to diagnose and treat diseases.

These high throughput screening techniques provide large data sets of gene expression information. Researchers have attempted to develop methods for organizing these data sets into patterns that are reproducibly diagnostic for diverse populations of individuals. One approach has been to pool data from multiple sources to form a combined data set and then to divide the data set into a discovery/training set and a test/validation set. However, both transcription profiling data and protein expression profiling data are often characterized by a large number of variables relative to the available number of samples.

Observed differences between expression profiles of specimens from groups of patients or controls are typically overshadowed by several factors, including biological variability or unknown sub-phenotypes within the disease or control populations, site-specific biases due to difference in study protocols, specimens handling, biases due to differences in instrument conditions (e.g., chip batches, etc), and variations due to measurement error. Some techniques attempt to correct to for bias in the data samples (which may result from, for example, having more of one class of sample represented in the data set than another class).

Several computer-based methods have been developed to find a set of features (markers) that best explain the difference between the disease and control samples. Some early methods included statistical tests such as LIMMA, the FDA approved mammaprint technique for identifying biomarkers relating to breast cancer, logistical regression techniques and machine learning methods such as support vector machines (SVM). Generally, from a machine learning perspective, the selection of biomarkers is typically a feature selection problem for a classification task. However, these early solutions faced several disadvantages. The signatures generated by these techniques were often not reproducible because the inclusion and exclusion of subjects can lead to different signatures. These early solutions also generated many false positive signatures and were not robust because they operated on datasets having small sample sizes and high dimensions.

Accordingly there is a need for improved techniques for identifying biomarkers for clinical diagnosis and/or prognosis, and more generally, for identifying data markers that can be used to classify elements in a data set into two or more classes.

SUMMARY

Described herein are systems, computer program products and methods for identifying data markers that can be used to classify elements in a data set into two or more classes. In particular, Applicants have recognized that a combination of methods and gene set data can provide better prediction of test data than an individual method alone. The computer systems and computer program products described herein implement methods that include one or more such techniques for classifying elements into two or more classes. In particular, biomarker signatures are generated using integrated dual ensemble and simulated annealing techniques. The techniques involve resampling a data set and predicting phenotypes using a dual ensemble method. In particular, the systems, computer program products, and methods described herein include forming a random vector indicative of a set of classification methods and data samples. The random vector is iteratively perturbed, and different objective values are computed that correspond to the different perturbations.

In certain aspects, the systems and methods described herein include means and methods for classifying a data set into two or more classes executed by a processor. The methods may comprise receiving a training data set. The training data set may be determined by separating an aggregate data set into a discovery (training) set and a validation (test) set. For example, the aggregate data set may include data that is pooled together from multiple sources, and the aggregate data set may be randomly split into training and test data sets. The methods may further comprise generating a first classifier for the training data set by applying a first machine learning technique to the training data set. For example, the machine learning technique may correspond to support vector machines (SVM) or any suitable technique for feature selection. A first training class set is generated by classifying the elements in the training data set according to the first classifier. In particular, the first classifier may correspond to a classification rule that assigns each sample in a data set to a physiological state (such as diseased or disease-free, for example). The first classifier may combine multiple classification methods such as SVN, network-based SVMs, neural network-based classifiers, logistic regression classifiers, decision tree-based classifiers, classifiers using a linear discriminant analysis technique, a random-forest analysis technique, any other suitable classification method, or any combination thereof.

A first objective value is computed based on the training class set. In particular, a binary generalized simulated annealing method may be used to compute the objective value. A random vector may include as its elements a set of parameters that define the classification technique to be used. The technique defined by the random vector is used to compute the first objective value. Then, for a plurality of iterations, a second machine learning technique is applied to the training data set to generate a second classifier for the training data set, and a second training class set is generated by classifying the elements in the training data set according to the second classifier. In particular, the second classifier may be generated by randomly perturbing the random vector used to define the first classifier, and using the random perturbation of the random vector to define the second classifier. Furthermore, a second objective value based on the second training class set is computed, and the first and second objective values are compared. Based on the comparison between the first and second objective values, the first training class set may be replaced with the second training class set, and the first objective value may be replaced by the second objective value, and the next iteration is begun. The iterations are repeated until a desired number of iterations is reached, and the first training class set is output.

In certain embodiments of the methods described above, the steps of the method are repeated for a plurality of training data sets, where each training data set in the plurality of training data sets is generated by bootstrapping an aggregate training data set. The bootstrapping may be performed with balanced samples or without balanced samples. Whether to bootstrap with balanced samples or without balanced samples may be determined by a binary element in the random vector, whose value may be updated when the random vector is perturbed. Other bootstrap parameters may be included as elements in the random vector, such as whether to sample a subset of samples from an aggregate set of samples with replacement or without replacement or a number of bootstraps. In certain embodiments of the methods, a sample is selected in a test data set, and the classifier corresponding to the output first training class set is used to predict a value associated with the selected sample. In certain embodiments of the methods, the second classifier is generated by applying a random vector to identify parameters for a classification scheme associated with the second classifier, the random vector including at least one binary value. In certain embodiments of the methods, the parameters of the random vector include a flag variable indicating whether to perform balanced bootstrapping, a number of bootstraps, a list of classification methods, a list of genes, or a combination thereof.

In certain embodiments of the methods, the step of computing the second objective value is based on a Matthew correlation coefficient. In particular, the objective value may correspond to a difference between 1 and the Matthew correlation coefficient of the results. The Matthew correlation coefficient is a performance metric that may be used as a composite performance score. In certain embodiments of the methods, the step of computing the second objective value comprises implementing a binary generalized simulated annealing method. In certain embodiments of the methods, the binary generalized simulated annealing method comprises locally perturbing one or more values of the random vector to identify parameters for the classification scheme. In certain embodiments of the methods, locally perturbing the one or more values of the random vector comprises randomly updating each element of the random vector to obtain an updated random vector, computing an updated second objective value using the updated random vector, and accepting the updated second objective value based on a comparison between a probability value and a random number. In certain embodiments of the methods, locally perturbing the one or more values of the random vector comprises changing one element of the random vector for each iteration.

In certain embodiments of the methods, the step of replacing the first training class set with the second training class set and replacing the first objective value with the second objective value is based on a cooling formula. In particular, it may be desirable to decrease the objective value in a binary generalized simulated annealing method by performing major perturbations on the random vector. In simulated annealing, an artificial temperature value is gradually reduced to simulate cooling. A visiting distribution is used in simulated annealing to simulate a trial jump distance from one point (i.e., a first set of values for the random vector) to another point (i.e., a second set of values for the random vector). The trial jump is accepted based on whether the second objective value is less than the first objective value and on an acceptance probability. The binary generalized simulated annealing method is used to identify a global minimum to minimize the objective value. In certain embodiments of the methods, the second classifier is selected from the group comprising linear discriminant analysis, support vector machine-based methods, random forest methods, and k nearest neighbor methods.

The computer systems of the present invention comprise means for implementing the various embodiments of the methods, as described above. For example, a computer program product is described, the product comprising computer-readable instructions that, when executed in a computerized system comprising at least one processor, cause the processor to carry out one or more steps of any of the methods described above. In another example, a computerized system is described, the system comprising a processor configured with non-transitory computer-readable instructions that, when executed, cause the processor to carry out any of the methods described above. The computer program product and the computerized methods described herein may be implemented in a computerized system having one or more computing devices, each including one or more processors. Generally, the computerized systems described herein may comprise one or more engines, which include a processor or devices, such as a computer, microprocessor, logic device or other device or processor that is configured with hardware, firmware, and software to carry out one or more of the computerized methods described herein. Any one or more of these engines may be physically separable from any one or more other engines, or may include multiple physically separable components, such as separate processors on common or different circuit boards. The computer systems of the present invention comprises means for implementing the methods and its various embodiments as described above. The engines may be interconnected from time to time, and further connected from time to time to one or more databases, including a perturbations database, a measurables database, an experimental data database and a literature database. The computerized system described herein may include a distributed computerized system having one or more processors and engines that communicate through a network interface. Such an implementation may be appropriate for distributed computing over multiple communication systems.

BRIEF DESCRIPTION OF THE DRAWINGS

Further features of the disclosure, its nature and various advantages, will be apparent upon consideration of the following detailed description, taken in conjunction with the accompanying drawings, in which like reference characters refer to like parts throughout, and in which.

DETAILED DESCRIPTION

To provide an overall understanding of the systems and methods described herein, certain illustrative embodiments will now be described, including systems and methods for identifying gene biomarker signatures. However, it will be understood by one of ordinary skill in the art that the systems and methods described herein may be adapted and modified for other suitable applications, such as any data classification application, and that such other additions and modifications will not depart from the scope thereof. Generally, the computerized systems described herein may comprise one or more engines, which include a processor or devices, such as a computer, microprocessor, logic device or other device or processor that is configured with hardware, firmware, and software to carry out one or more of the computerized methods described herein.

The systems and methods described herein include techniques for generating biomarker signatures with integrated dual ensemble and simulated annealing techniques. The techniques involve resampling a data set and predicting phenotypes using a dual ensemble method. In particular, the systems and methods described herein include forming a random vector indicative of a set of classification methods, data samples, and iteratively perturbing the random vector and computing different objective values corresponding to the different perturbations.

Figure 1:
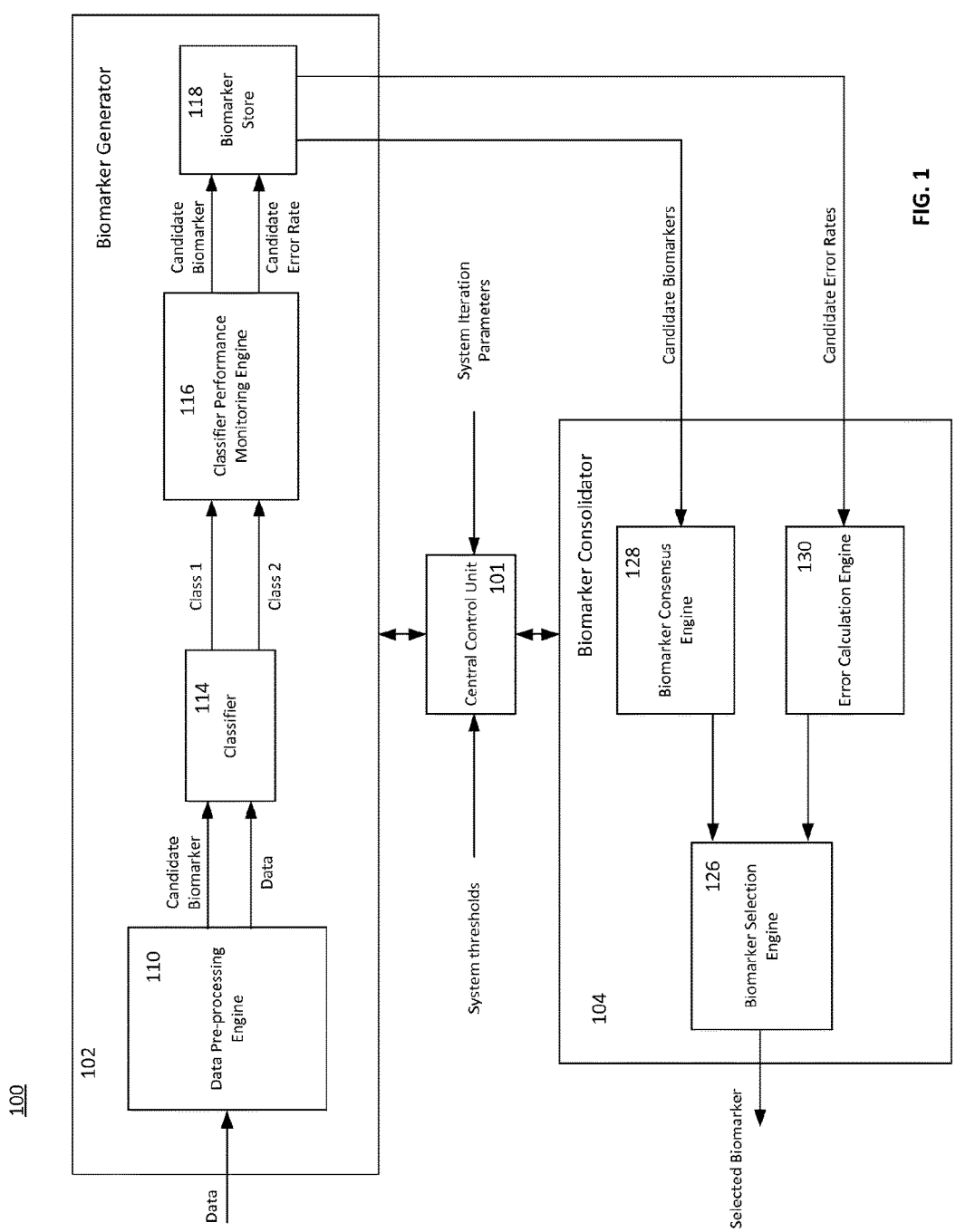
FIG. 1 depicts an exemplary system for identifying one or more biomarker signatures.

FIG. 1 depicts an exemplary system 100 for identifying one or more biomarker signatures, in which the classification techniques disclosed herein may be implemented. The system 100 includes a biomarker generator 102 and a biomarker consolidator 104. The system 100 further includes a central control unit (CCU) 101 for controlling certain aspects of the operation of the biomarker generator 102 and the biomarker consolidator 104. During operation, data such as gene expression data is received at the biomarker generator 102. The biomarker generator 102 processes the data to generate a plurality of candidate biomarkers and corresponding error rates. The biomarker consolidator 104 receives these candidate biomarkers and error rates and selects a suitable biomarker having an optimal performance measure and size.

The biomarker generator 102 includes several components for processing data and generating a set of candidate biomarkers and candidate error rates. In particular, the biomarker generator 102 includes a data pre-processing engine 110 for splitting the data into a training data set and a test data set. The biomarker generator 102 includes a classifier 114 for receiving the training data set and the test data set and classifying the test data set into one of two or more classes (e.g., disease data and non-diseased, susceptible and immune, etc.). The biomarker generator 102 includes a classifier performance monitoring engine 116 for determining the performance of the classifier as applied to the test data selected by the data pre-processing engine 110. The classifier performance monitoring engine 116 identifies candidate biomarkers based on the classifier (e.g., the components of the elements of the data set that are most important to the classification) and generates performance measures, which may include candidate error rates, for one or more candidate biomarkers. The biomarker generator 102 further includes a biomarker store 118 for storing one or more candidate biomarkers and candidate performance measures.

The biomarker generator may be controlled by the CCU 101, which in turn may be automatically controlled or user-operated. In certain embodiments, the biomarker generator 102 may operate to generate a plurality of candidate biomarkers, each time splitting the data randomly into training and test data sets. To generate such a plurality of candidate biomarkers, the operation of the biomarker generator 102 may be iterated a plurality of times. CCU 101 may receive one or more system iteration parameters including a desired number of candidate biomarkers, which in turn may be used to determine the number of times the operation of the biomarker generator 102 may be iterated. The CCU 101 may also receive other system parameters including a desired biomarker size which may be representative of the number of components in a biomarker (e.g., the number of genes in a biomarker gene signature). The biomarker size information may be used by the classifier performance monitoring engine 116 for generating candidate biomarkers from the training data. The operation of the biomarker generator 102 and the classifier 114 in particular, are described in more detail with reference to FIGS. 2-8.

The biomarker generator 102 generates one or more candidate biomarkers and candidate error rates, which is used by the biomarker consolidator 104 for generating robust biomarkers. The biomarker consolidator 104 includes a biomarker consensus engine 128 which receives a plurality of candidate biomarkers and generates a new biomarker signature having the most frequently occurring genes across the plurality of candidate biomarkers. The biomarker consolidator 104 includes an error calculation engine 130 for determining an overall error rate across the plurality of candidate biomarkers. Similar to the biomarker generator 102, the biomarker consolidator 104 may also be controlled by the CCU 101, which in turn may be automatically controlled or user-operated. The CCU 101 may receive and/or determine a suitable threshold values for the minimum biomarker size, and use this information to determine the number of iterations to operate both the biomarker generator 102 and the biomarker consolidator 104. In one embodiment, during each iteration, the CCU 101 decreases the biomarker size by one and iterates both the biomarker generator 102 and the biomarker consolidator 104 until the threshold is reached. In such an embodiment, the biomarker consensus engine 128 outputs a new biomarker signature and a new overall error rate for each iteration. The biomarker consensus engine 128 thus outputs set of new biomarker signatures each having a different size varying from the threshold value up to a maximum biomarker size. The biomarker consolidator 104 further includes a biomarker selection engine 126 which reviews the performance measure or error rate of each of these new biomarker signatures and selects the optimal biomarker for output.

The data preprocessing engine 110 receives one or more datasets. Generally, the data may represent expression values of a plurality of different genes in a sample, and/or a variety of a phenotypic characteristics such as levels of any biologically significant analyte. In certain embodiments, the data sets may include expression level data for a disease condition and for a control condition. As used herein, the term "gene expression level" may refer to the amount of a molecule encoded by the gene, e.g., an RNA or polypeptide, or the amount of a miRNA. The expression level of an mRNA molecule may include the amount of mRNA (which is determined by the transcriptional activity of the gene encoding the mRNA) and the stability of the mRNA (which is determined by the half-life of the mRNA). The gene expression level may also include the amount of a polypeptide corresponding to a given amino acid sequence encoded by a gene. Accordingly, the expression level of a gene can correspond to the amount of mRNA transcribed from the gene, the amount of polypeptide encoded by the gene, or both. Expression levels of a gene may be further categorized by expression levels of different forms of gene products. For example, RNA molecules encoded by a gene may include differentially expressed splice variants, transcripts having different start or stop sites, and/or other differentially processed forms. Polypeptides encoded by a gene may encompass cleaved and/or modified forms of polypeptides. Polypeptides can be modified by phosphorylation, lipidation, prenylation, sulfation, hydroxylation, acetylation, ribosylation, farnesylation, addition of carbohydrates, and the like. Further, multiple forms of a polypeptide having a given type of modification can exist. For example, a polypeptide may be phosphorylated at multiple sites and express different levels of differentially phosphorylated proteins. The levels of each of such modified polypeptides may be separately determined and represented in the datasets.

Figure 2:
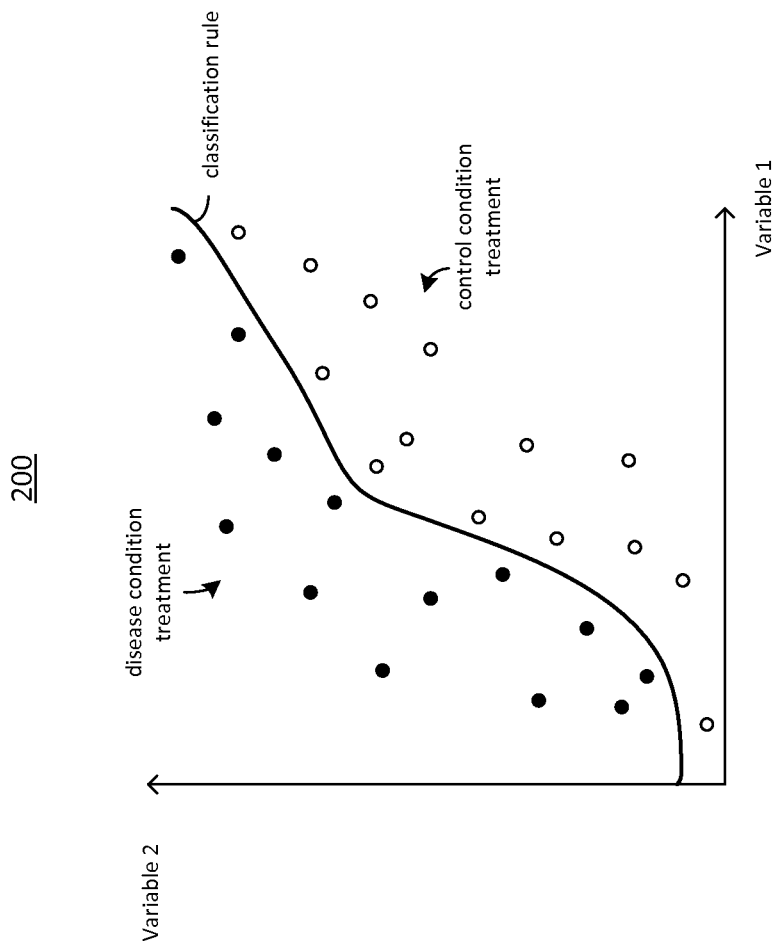
FIG. 2 is a graph depicting the classification of data samples and the determination of a classification rule.

The classifier 114 receives one or more sets of data from the data pre-processing engine 110. In certain embodiments, the classifier 114 generates a classification rule to classify the data. FIG. 2 depicts, graphically such a classification rule 200. The classifier 114 may apply the classification rule to assign the data sets to either one of two classes. For example, the classifier 114 may apply the classification to assign data sets to either disease or control.

In certain embodiments, as is described in relation to FIGS. 3-8, the classifier 114 uses a dual ensemble technique combined with a generalized simulated annealing method to generate a classification rule. In particular, the classifier 114 may combine multiple classification methods such as support vector machine (SVM), network based SVMs, neural network-based classifiers, logistic regression classifier, decision tree-based classifier, classifiers employing a linear discriminant analysis technique, and/or a random-forest analysis technique, or any other suitable classification method. The ensemble classification strategy may use a voting process across multiple diverse classification methods to identify an optimal classification. By incorporating multiple classification methods, ensemble techniques reduce the potential for overfitting to a small data set. In this way, small data sets may be used more efficiently by using an ensemble technique compared to other techniques. Furthermore, using an ensemble of multiple classification methods allows for enhanced classification compared to using a single classification method, especially when the multiple classification methods in the ensemble are diverse from one another.

In addition, the data received from the data pre-processing engine 110 may be perturbed to further increase overall diversity while providing better classification accuracy. Examples of perturbation of data are described in more detail in relation to FIGS. 4, 7, and 8.

As described herein, the classifier 114 uses an ensemble technique and a generalized simulating annealing method to generate a classification rule and are described in relation to applications in bioinformatics. However, the systems and methods described herein may generally be applied to any large scale computational technique such as feature selection or extraction.

The classifier performance monitoring engine 116 may analyze the performance of the classifier 114 using a suitable performance metric. In particular, when analyzing the performance of the classifier 114, the classifier performance monitoring engine 116 may be analyzing the robustness or performance of one or more candidate biomarkers. In certain embodiments, the performance metric may include an error rate. The performance metric may also include the number of correct predictions divided by the total predictions attempted. The performance metric may be any suitable measure without departing from the scope of the present disclosure. The candidate biomarker and the corresponding performance metric may be stored in biomarker store 118.

In certain embodiments the gene expression level in a cell or tissue may be represented by a gene expression profile. Gene expression profiles may refers to a characteristic representation of a gene's expression level in a specimen such as a cell or tissue. The determination of a gene expression profile in a specimen from an individual is representative of the gene expression state of the individual. A gene expression profile reflects the expression of messenger RNA or polypeptide or a form thereof encoded by one or more genes in a cell or tissue. An expression profile may generally refer to a profile of biomolecules (nucleic acids, proteins, carbohydrates) which shows different expression patterns among different cells or tissue. A data sample representing a gene expression profile may be stored as a vector of expression levels, with each entry in the vector corresponding to a particular biomolecule or other biological entity.

In certain embodiments, the data sets may include elements representing gene expression values of a plurality of different genes in a sample. In other embodiments, the data set may include elements that represent peaks detected by mass spectrometry. Generally, each data set may include data samples that each correspond to one of a plurality of biological state classes. For example, a biological state class can include, but is not limited to: presence/absence of a disease in the source of the sample (i.e., a patient from whom the sample is obtained); stage of a disease; risk for a disease; likelihood of recurrence of disease; a shared genotype at one or more genetic loci (e.g., a common HLA haplotype; a mutation in a gene; modification of a gene, such as methylation, etc.); exposure to an agent (e.g., such as a toxic substance or a potentially toxic substance, an environmental pollutant, a candidate drug, etc.) or condition (temperature, pH, etc); a demographic characteristic (age, gender, weight; family history; history of preexisting conditions, etc.); resistance to agent, sensitivity to an agent (e.g., responsiveness to a drug) and the like.

Data sets may be independent of each other to reduce collection bias in ultimate classifier selection. For example, they can be collected from multiple sources and may be collected at different times and from different locations using different exclusion or inclusion criteria, i.e., the data sets may be relatively heterogeneous when considering characteristics outside of the characteristic defining the biological state class. Factors contributing to heterogeneity include, but are not limited to, biological variability due to sex, age, ethnicity; individual variability due to eating, exercise, sleeping behavior; and sample handling variability due to clinical protocols for blood processing. However, a biological state class may comprise one or more common characteristics (e.g., the sample sources may represent individuals having a disease and the same gender or one or more other common demographic characteristics).

In certain embodiments, the data sets from multiple sources are generated by collection of samples from the same population of patients at different times and/or under different conditions.

In certain embodiments, a plurality of data sets is obtained from a plurality of different clinical trial sites and each data set comprises a plurality of patient samples obtained at each individual trial site. Sample types include, but are not limited to, blood, serum, plasma, nipple aspirate, urine, tears, saliva, spinal fluid, lymph, cell and/or tissue lysates, laser microdissected tissue or cell samples, embedded cells or tissues (e.g., in paraffin blocks or frozen); fresh or archival samples (e.g., from autopsies). A sample can be derived, for example, from cell or tissue cultures in vitro. Alternatively, a sample can be derived from a living organism or from a population of organisms, such as single-celled organisms.

In one example, when identifying biomarkers for a particular cancer, blood samples for might be collected from subjects selected by independent groups at two different test sites, thereby providing the samples from which the independent data sets will be developed.

In some implementations, the training and test sets are generated by the data pre-processing engine 110, which receives bulk data and splits the bulk data into a training data set and a test data set. In certain embodiments, the data pre-processing engine 110 randomly splits the data into these two groups. Randomly splitting the data may be desirable for predicting classes and generating robust gene signature. In other embodiments, the data pre-processing engine 110 splits the data into two or more groups based on the type or label of the data. Generally, the data can be split into a training data set and a test data set in any suitable way as desired without departing from the scope of the present disclosure. The training data set and the test data set may have any suitable size and may be of the same or different sizes. In certain embodiments, the data pre-processing engine 110 may discard one or more pieces of data prior to splitting the data into the training and test data sets. In certain embodiments, the data pre-processing engine 110 may discard one or more pieces of data from the training data set and/or the test data set prior to any further processing.

The classifier 114 may receive one or more candidate biomarkers and one or more sets of data from the data pre-processing engine 110. The classifier 114 may apply the classification rule to assign data sets to either one of two classes. For example, the classifier 114 may apply the classification to assign data sets to either disease or control. In certain embodiments, the classifier 114 may include a support vector machine (SVM) classifier, network based SVMs, neural network-based classifiers, logistic regression classifier, decision tree-based classifier, classifiers employing a linear discriminant analysis technique, and/or a random-forest analysis technique. The operation of the classifier 114 and its respective engines are described in more detail with reference to FIGS. 2-8.

The classifier performance monitoring engine 116 may analyze the performance of the classifier 114 using a suitable performance metric. In particular, when analyzing the performance of the classifier 114, the classifier performance monitoring engine 116 may be analyzing the robustness or performance of one or more candidate biomarkers. In certain embodiments, the performance metric may include an error rate. The performance metric may also include the number of correct predictions divided by the total predictions attempted. The performance metric may be any suitable measure without departing from the scope of the present disclosure. The candidate biomarker and the corresponding performance metric may be stored in biomarker store 118.

As noted earlier, the CCU 101 may also control the operation of the biomarker consolidator 104 for generating a suitable and robust biomarker based on the candidate biomarkers generated and stored in the biomarker generator 102. The biomarker consolidator 104 includes a biomarker consensus engine 128, which receives one or more candidate biomarkers from the biomarker store 118. The biomarker consensus engine 128 may select frequently occurring genes within the one or more candidate biomarkers for a new biomarker signature. The new biomarker signature may include an N number of genes, where N is a desired size of the biomarker, the maximum allowed size of the biomarker, a minimum allowed size of the biomarker or a size between the maximum and minimum sizes. In certain embodiments, the number N may be user-selectable and may be adjustable as desired.

Figure 3:
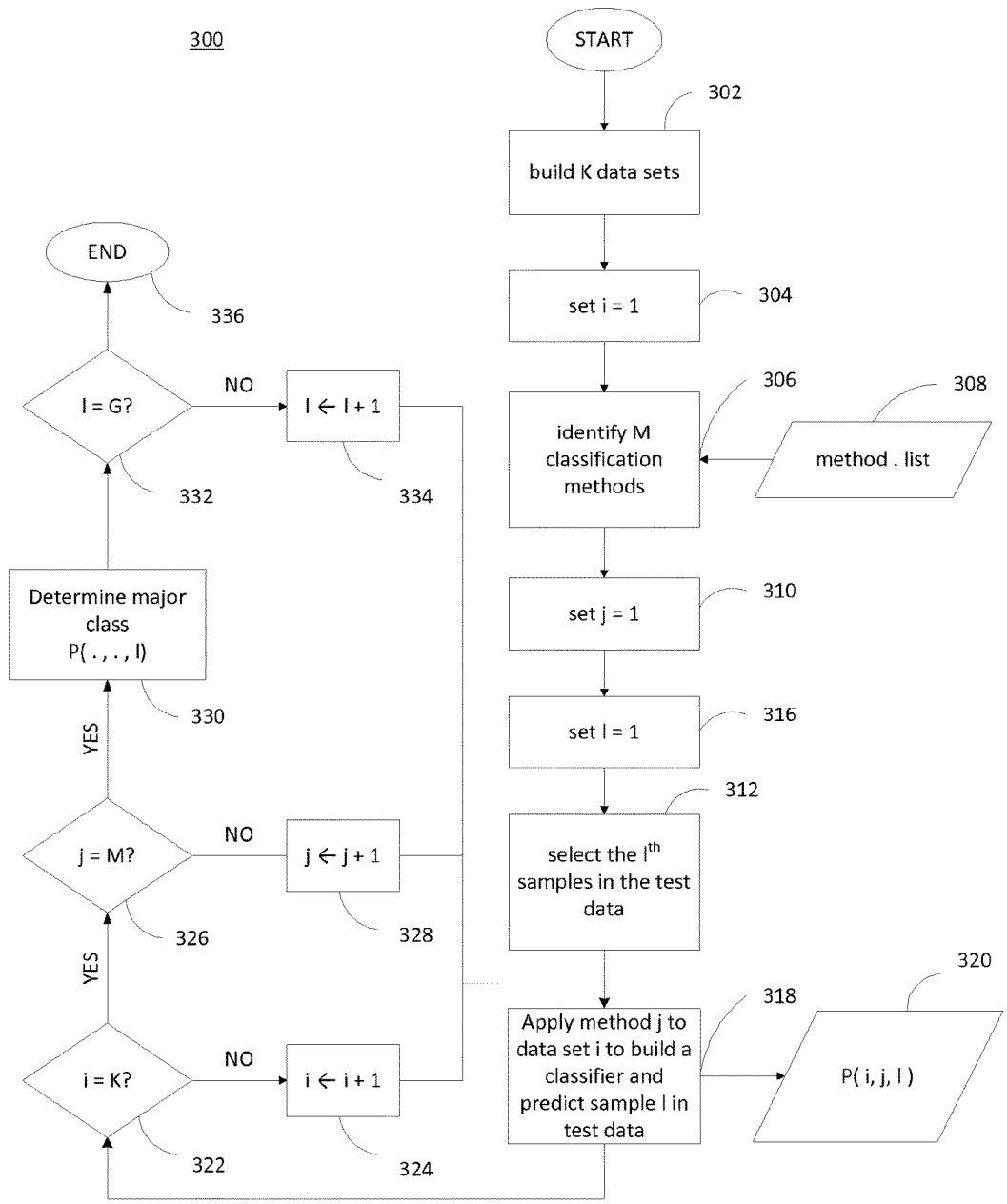
FIG. 3 is a flow diagram of a dual ensemble method.

FIG. 3 is a flow diagram of a method 300 used by the classifier 114 to predict, using a voting method, a phenotype class. As shown, the method 300 includes the steps of building K data sets (step 302), identifying M classification methods (step 306), and identifying G samples in each of the K data sets (step 312). The method 300 further includes three iteration loops, including iterating over the K data sets, the M classification methods, and the G samples, where G is the sample size of the test data set. In particular, in each iteration, a classification method j is applied to a sample 1 in a dataset i to predict a phenotype (step 318), where i=1, 2, . . . K, j=1, 2, . . . M, and l=1, 2, . . . G.

At step 302, the classifier 114 builds K data sets. The classifier may use the method depicted in FIG. 4 to build K data sets. In particular, the classifier 114 may use boot strapping aggregation methods to form multiple data sets of a complete data set. At step 304, a data set iteration parameter i, representative of a label applied to a data set, is initialized to 1.

At step 306, the classifier 114 identifies M classification methods. The classifier 114 may receive the classification methods from an external source, or the classification methods may be generated by the classifier 114 based on some input. As an example, the classifier 114 may identify the M classification methods based on a list of methods 308. Examples of methods include linear discriminant analysis, support vector machine-based methods, random forest methods (Breiman, *Machine Learning*, 45(1):5-32 (2001)), PAMR (Tibshirani et al., *Proc Natl Acad Sci USA*, 99(10): 6567-6572 (2002)) or k nearest neighbor methods (Bishop, Neural Networks for Pattern Recognition, ed. O.U. Press, 1995). Any number of classification methods may be used and considered. At step 310, a method iteration parameter j, representative of a label applied to a classification method, is initialized to 1. At step 316, a sample iteration parameter 1, representative of a label applied to a data sample, is initialized to 1. Each data sample may be representative of a person, a gene, or any other suitable data point.

At step 312, the classifier 114 selects the $1^{th}$ samples in the test data set, and at step 318, the classifier 114 applies a classification method j to a data set i to build a classifier and predict a sample 1 in the test data. The prediction of sample 1 may correspond to the prediction of a phenotype. In some embodiments, the phenotype may be a flag variable (i.e., 1 if it is predicted that the person expresses the phenotype, and 0 otherwise). However, in general, the phenotype may take on any number of values. In particular, the phenotype prediction may be stored as a value in a three dimensional matrix P(i,j,l) 320.

At decision block 322, the classifier 114 determines whether the last data set has been considered, or equivalently, whether i=K. If i is less than K, the classifier 114 increments the data set iteration parameter i at step 324 and returns to step 318 to predict the phenotype for the new data set.

After all K data sets have been considered, the classifier 114 proceeds to decision block 326 to determine whether the last classification method has been applied, or equivalently, whether j=M. If j is less than M, the classifier 114 increments the method iteration parameter j at step 328 and returns to step 318 to predict the phenotype for the new classification method.

After all K data sets have been considered and all M classification methods have been applied, the classifier 114 has K×M phenotype predictions for the current data sample 1. These phenotype predictions may be thought of as votes, and any sort of vote counting method may be used to arrive at a composite vote representative of the set of K×M phenotype predictions.

At decision block 332, the classifier determines whether all G data samples have been considered, or equivalently, whether 1=G.

Figure 4:
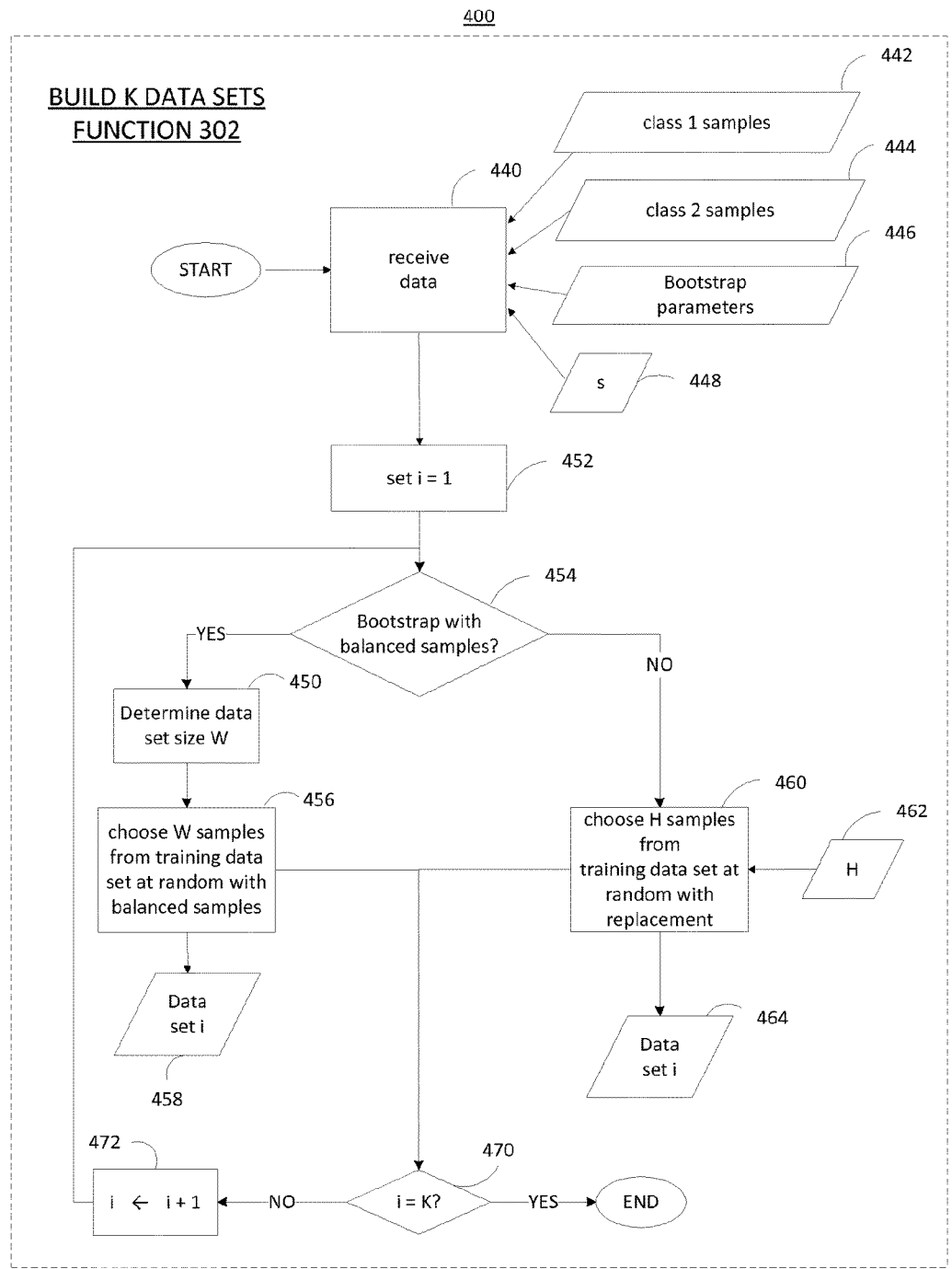
FIG. 4 is a flow diagram of a method for building data sets.

FIG. 4 is a flow diagram of a method 400 for building data sets, and may be used by the classifier 114 at step 302 in FIG. 3. In general, the method 400 provides a way to generate multiple data sets that are each subsets of a larger data set. A data subset may be formed by bootstrap aggregating ("bagging") methods, which involve randomly selecting a subset of samples in a large data set. The subset of samples may be selected with or without replacement. As shown, the method 400 includes the steps of receiving data (step 440) and determining whether it is desirable to perform bootstrapping without replacement (decision block 454). If so, a number W of samples may be randomly selected from each class (step 456) to form a data set. Alternatively, a number H of samples may be randomly selected with replacement from training data (steps 460 and 466) to form a data set. The value for H may correspond to a sample size of the training data set. The above steps are repeated until each data set i described in relation to FIG. 3 has been considered.

At step 440, the classifier 114 receives data. The data may include samples sorted into two classes (i.e., class 1 samples 442 and class 2 samples 444), bootstrap parameters 446, and a ratio s 448, between the size of a resulting data set i (i.e., a data subset) and the size of a class (i.e., class 1 or class 2). As an example, the bootstrap parameters 446 may include a variable indicative of whether to bootstrap with or without replacement and the number of bootstrap data sets (i.e., K). The data 442, 444, 446, and 448 may be used by the classifier 114 to build the K data sets.

At step 452, a data set iteration parameter i is initialized to 1. The iteration parameter i is representative of a label applied to a data set.

At decision block 454, the classifier 114 determines whether it is desirable to bootstrap with balanced samples. In particular, the classifier 114 may use a variable such as a bootstrap parameter 446 to determine whether bootstrapping with balanced samples is desirable. In general, bootstrapping with balanced samples ensures that the total number of occurrences of each sample point across all K data sets is the same.

If balanced bootstrapping is desirable, the classifier 114 proceeds to step 450 to determine a data set size W. In particular, the size W may be dependent on the ratio s 448, such as W=min {size(class 1 samples), size(class 2 samples) }*s, for example. In particular, the ratio s may be a value between 0 and 1. At step 456, W samples from the training data set are randomly selected with balanced samples, forming a data set i 458. When the iteration parameter i is greater than 1, the selection of W samples at step 456 may be dependent on previously formed data sets, such that the bootstrapping is balanced.

Alternatively, if bootstrapping with balanced samples is not desirable, the classifier 114 proceeds to step 460 to randomly select H samples from the training data set with replacement. The selected samples form the data set i 464.

As is depicted in FIG. 4, balanced bootstrapping results in data sets with size W, while bootstrapping the data without balanced samples results in data sets with size H. However, in general, any suitable combination of methods may be used, such as bootstrapping without balanced samples for data sets with size W, or balanced bootstrapping for data sets with size H. In addition, bootstrapping without replacement methods may also be used.

After the current data set i has been formed, the classifier 114 proceeds to decision block 470 to determine whether the last data set has been formed, or equivalently, whether i=K. If not, at step 472, the data set iteration parameter i is incremented, and the classifier 114 proceeds to decision block 454 to begin forming the next data set.

Figure 5:
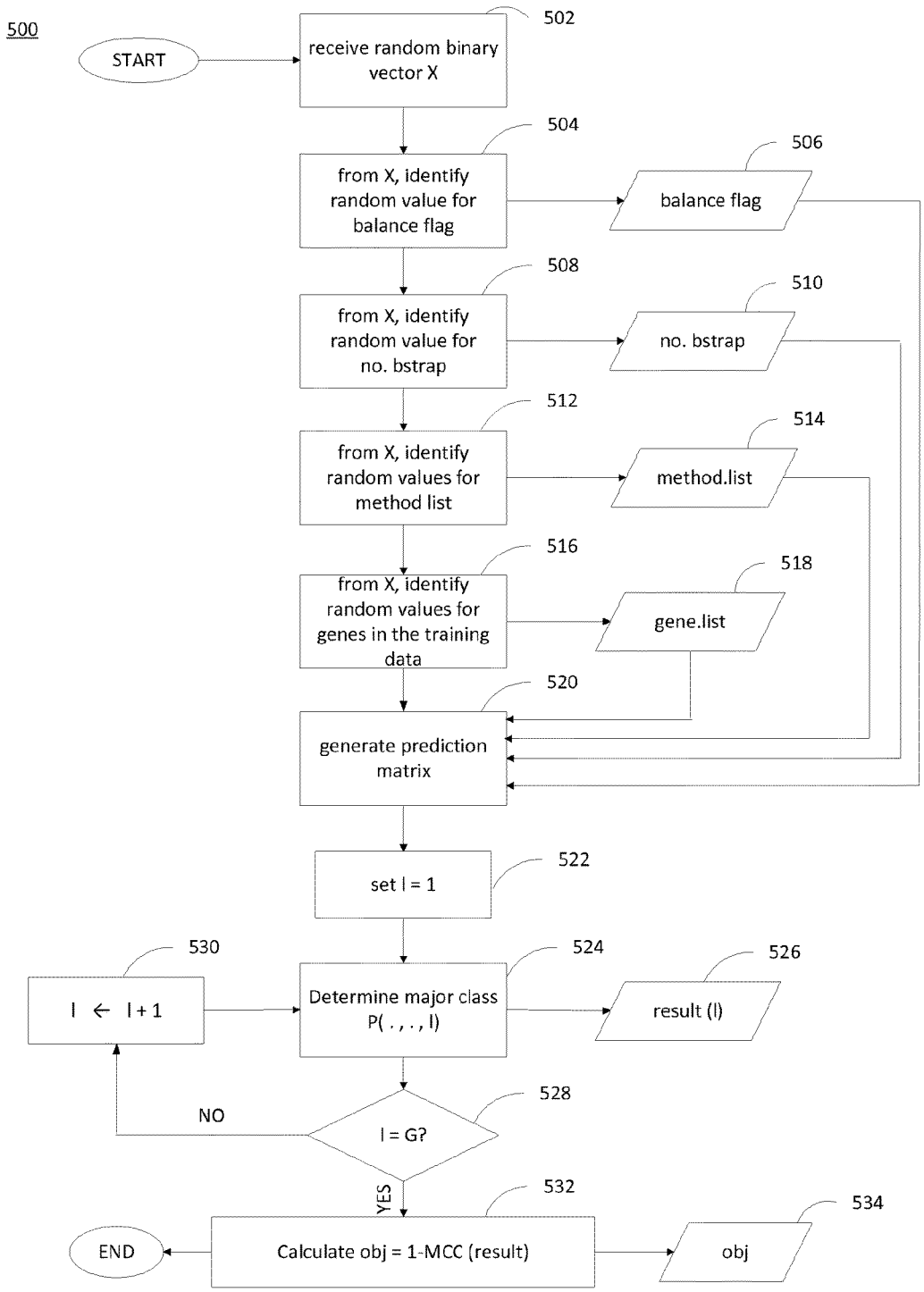
FIG. 5 is a flow diagram of a method for generating a result vector and objective value.

FIG. 5 is a flow diagram of a method for generating a result vector and objective value. In general, the method 500 provides a way to calculate an objective value corresponding to a random vector X. As depicted in the method 500, the random vector X is a binary vector X and includes information regarding whether to bootstrap with replacement (506), the number of bootstraps (510), a list of the classification methods (514), and a list of data samples (518). Based on these data, a prediction matrix is formed (step 520), and a major class is determined (step 524). The classifier 114 iterates over the data samples until all data samples have been considered, and an objective value is computed based on the determined major classes for the data samples (step 532).

At step 502, the classifier 114 receives a binary random vector X. In an example, the vector X may be a list of binary values. The binary values may be indicative of whether to perform balanced bootstrapping, a number of bootstraps (i.e., K), a list of classification methods, and/or a list of genes. In particular, the number of bootstraps may take on either a zero value or a non-zero value (i.e., 60, for example). In this case, the binary value in the vector X corresponding to the number of bootstraps may be indicative of whether the number of bootstraps is zero or non-zero. The random values may be generated by a random value generator or any other suitable method for generating random values. As is described herein, the random vector X is a binary vector, meaning each value in the vector is one of two values (i.e., 0 or 1). However, in general, the values in the random vector X can be one of any number of values. The classifier 114 identifies various parameters based on the random values in the vector X. As examples, the classifier 114 identifies a value for a flag 506 indicative of whether to sample with balanced samples at step 504, a number of bootstraps 510 at step 508, a list of classification methods 514 at step 512, and a list of genes 518 at step 516.

Based on the identified various parameters, at step 520, the classifier 114 generates a prediction matrix.

At step 522, a sample iteration parameter 1, representative of a label applied to a data sample, is initialized to 1.

At step 524, the classifier 114 determines the major class P(., ., 1). In particular, the classifier 114 may parse through the steps 302-330 in method 300 to identify K×M phenotype predictions, and take a majority vote on the K×M predictions to determine the major class P(., ., 1). In general, any other suitable method for generating a composite prediction based on the set of K×M predictions may be used to determine the major class. The major class may be stored as an entry in a result vector 526.

At decision block 528, the classifier 114 determines whether the sample iteration parameter 1 is equal to the total number of data samples G. If not, the iteration parameter 1 is incremented at step 530, and the major class is determined for the next data sample.

After the major class has been determined for each sample in the set of G samples, the classifier 114 proceeds to step 532 to calculate an objective value. The objective value may be calculated based on the resultant set of entries in the result vector 526. In particular, a composite performance score may be an average of the performance metrics. As depicted in the method 500, the objective value 532 is calculated as the difference between 1 and the Matthew correlation coefficient (MCC) of the results. The MCC is a performance metric that may be used as a composite performance score. In particular, the MCC is a value between −1 and +1 and is essentially a correlation coefficient between the observed and predicted binary classifications. The MCC may be computed using the following equation:

$$MCC = \frac{TP*TN - FP*FN}{\sqrt{(TP+FP)*(TP+FN)*(TN+FP)*(TN+FN)}}$$

where TP: true positive; FP: false positive; TN: true negative; FN: false negative. However, in general, any suitable technique for generating a composite performance metric based on a set of performance metrics may be used to calculate the objective value.

Figure 6:
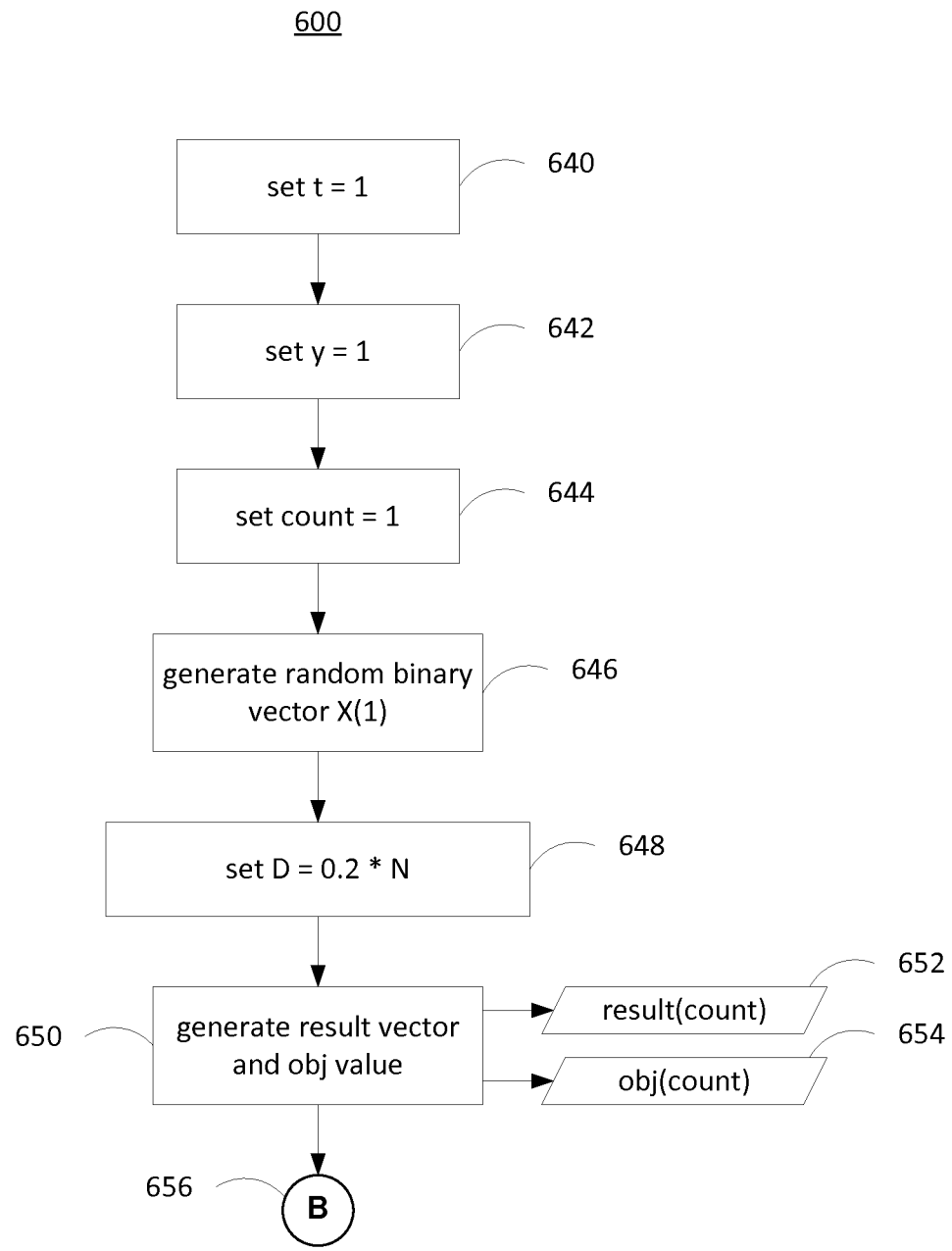
FIG. 6 is a flow diagram of a method for initializing a binary generalized simulated annealing method.
Figure 7:
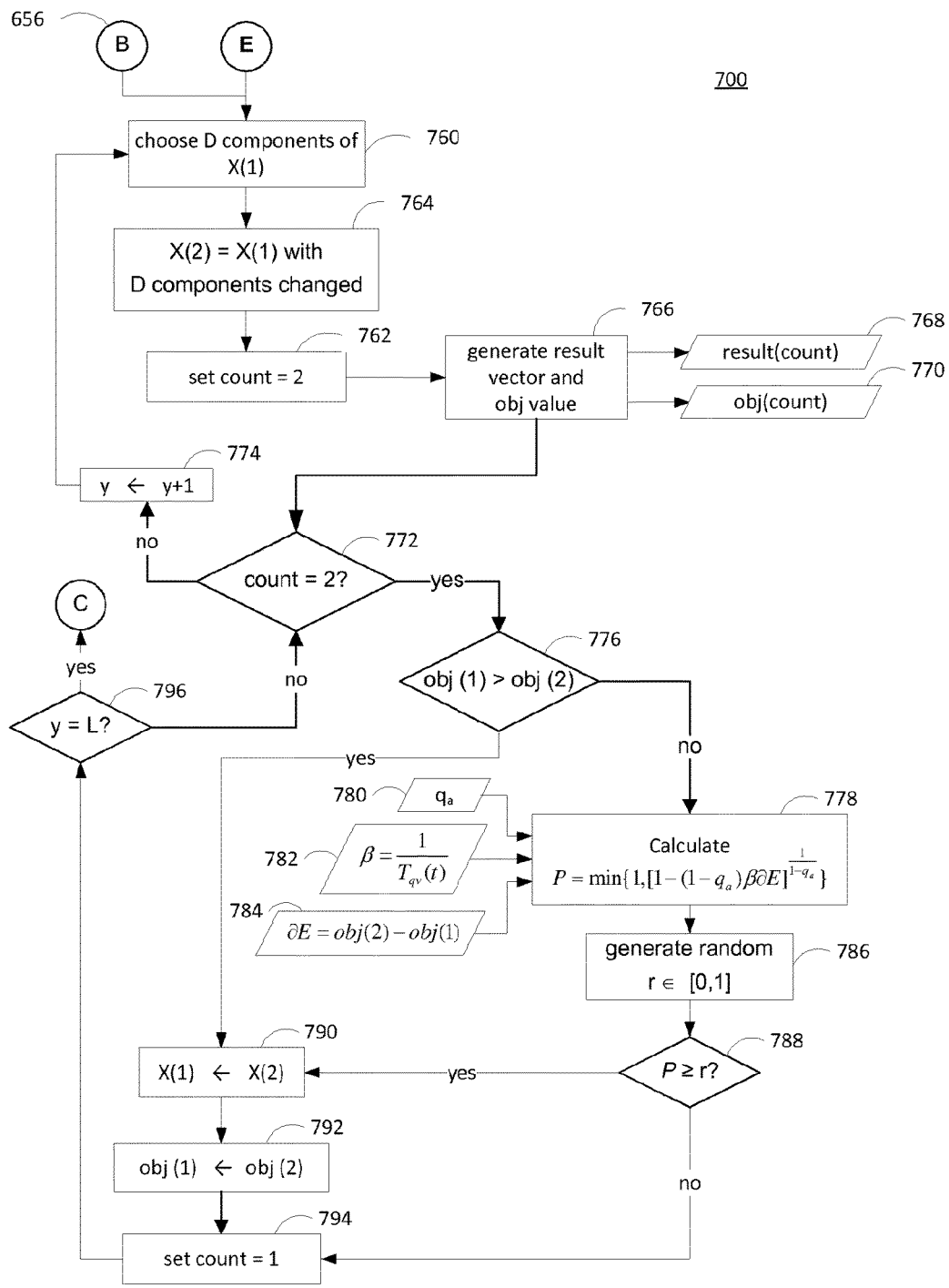
FIG. 7 is a flow diagram of a method for decreasing an objective value in a binary generalized simulated annealing method.
Figure 8:
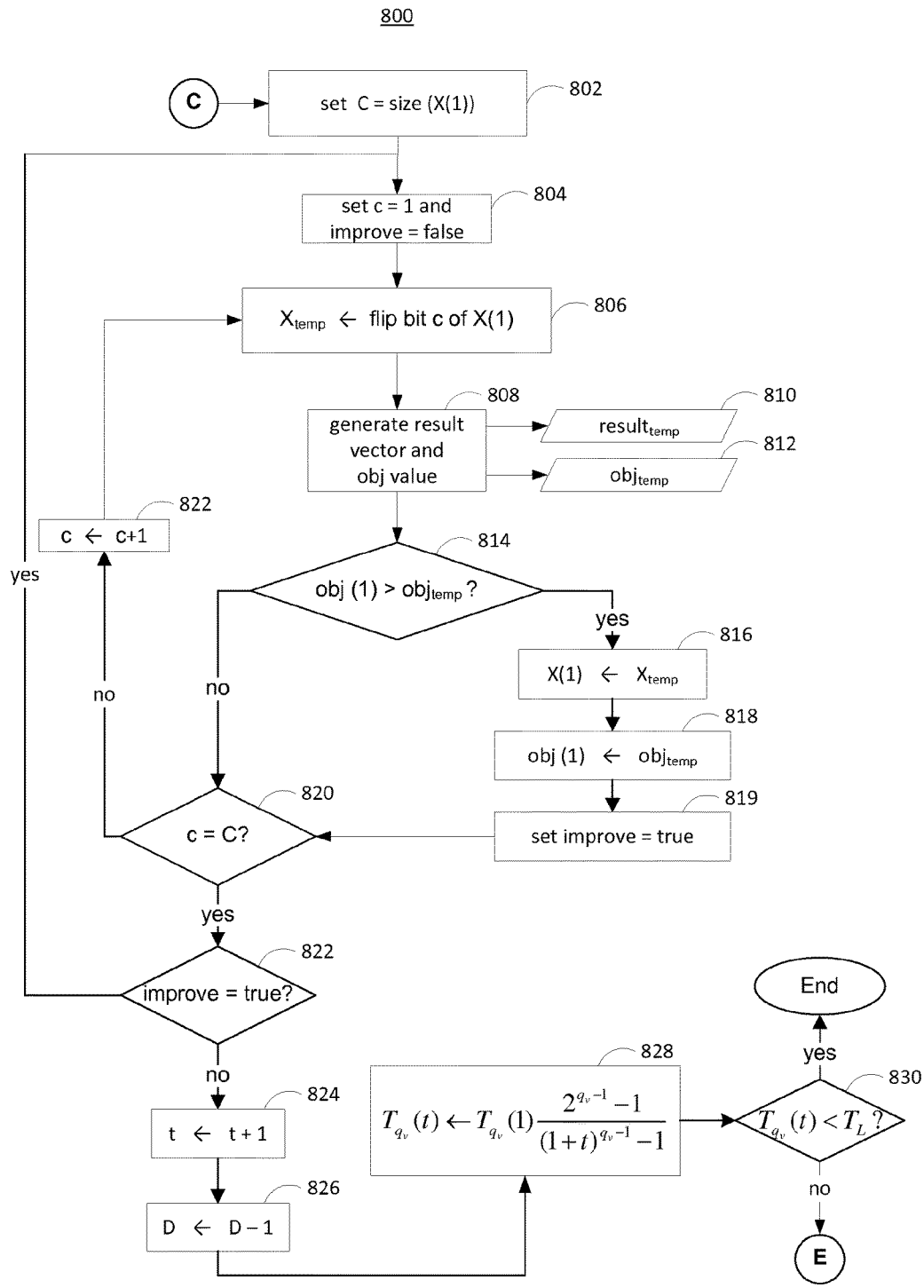
FIG. 8 is a flow diagram of a method for further decreasing an objective value in a binary generalized simulated annealing method.

FIGS. 6-8 are flow diagrams of methods for parsing through the steps of a binary generalized simulated method. In general, the binary generalized simulated annealing method may be used to identify an optimal value (i.e., a global minimum) for the objective value as described in FIG. 5. As described herein, a binary generalized simulated annealing method is used in conjunction with the dual ensemble method described in FIG. 3. In particular, a random vector X as described in FIG. 5 is perturbed in various ways to identify an optimal objective value. FIG. 6 is a flow diagram for initializing the binary generalized simulated annealing method. FIG. 7 is a flow diagram for randomly perturbing various components of the random vector X to decrease the objective value. FIG. 8 is a flow diagram for locally perturbing the random vector X to further decrease the objective value. In other words, the method depicted in FIG. 7 generates major perturbations of the random vector X, while the method depicted in FIG. 8 generates minor perturbations of the random vector X.

FIG. 6 is a flow diagram of a method 600 for initializing a binary generalized simulated annealing method. The method 600 initializes several parameters and generates a random binary vector X(1). In particular, at steps 640, 642, and 644, the classifier 114 initializes parameters t, y, and count to 1, respectively. The parameter t corresponds to a time interval, and is incremented when a suitable objective value is determined, as is described in relation to FIGS. 7 and 8. The iteration parameter y corresponds to a number of major perturbations that are performed, and is described in more detail in relation to FIG. 7. The parameter count corresponds to a parameter for keeping track of whether a perturbed version of the current vector X has been generated, and is described in more detail in relation to FIG. 7. At step 646, the classifier 114 generates a random binary vector X.

At step 648, a parameter D is set. The parameter D corresponds to a number of components in X that will be selected to be perturbed. In particular, at step 648, the parameter D is set to 0.2*C, where C corresponds to the length of binary vector X.

At step 650, the classifier 114 generates a result vector and an objective value. In particular, the classifier 114 may use the method depicted in FIG. 5 to generate a result vector 526 and an objective value 534. However, in general, any suitable method to determine an objective value representative of a composite performance metric may be used. After generating an objective value, the classifier 114 proceeds to steps in FIG. 7 to decrease the objective value by perturbing the random vector X.

FIG. 7 is a flow diagram of a method for decreasing an objective value in a binary generalized simulated annealing method by performing major perturbations on a vector X. In the simulating annealing method, an artificial temperature is introduced (T(t=1)) and gradually reduced to simulate cooling. A visiting distribution is used in simulated annealing to simulate a trial jump distance from one point to a second point (i.e., from one random vector X(1) to another random vector X(2)). The trial jump is accepted based on whether the resulting objective value corresponding to the random vector X(2) is smaller than the objective value corresponding to the random vector X(1) and on an acceptance probability as is defined below. As is described herein, a binary generalized simulated annealing method is used to locate a global minimum (i.e., to minimize the objective value). However, in general, any suitable algorithm may be used, such as steepest descent, conjugate gradient, simplex, and Monte Carlo methods.

After initializing the simulation using the method depicted in FIG. 6, the classifier 114 begins at step 760 to select D components of the vector X(1). The D components of the vector X(1) may be selected randomly, or any other suitable method of selecting D components of the vector X(1) may be performed. At step 762, the count variable is set to 2. At step 764, a second random binary vector X(2), corresponding to the original random vector X(1) with the D components changed, is generated.

At step 766, the classifier 114 generates a result vector 768 and an objective value 770 for the second vector X(2). In particular, the classifier 114 may use the method depicted in FIG. 5 to generate a result vector and an objective value. However, in general, any suitable method to determine an objective value representative of a composite performance metric may be used.

After generating the second result vector and the second objective value, the classifier determines that the count variable is equal to 2 at decision block 772 and proceeds to decision block 776 to compare the first objective value (i.e., corresponding to the random vector X(1)) and the second objective value (i.e., corresponding to the random vector X(2)).

If the second objective value is not smaller than the first objective value, this means that the first vector X(1) resulted in a better or equal correlation as the second vector X(2). In this case, the classifier proceeds to step 778 to compute a probability P. In particular, the probability P corresponds to a probability of accepting the second objective value, and is based on the equation:

$$P = \min\left\{1, [1 - (1 - q_a)\beta \partial E]^{\frac{1}{1-q_a}}\right\}$$

where $\partial E = obj(2) - obj(1)$ $$\beta = \frac{1}{T_{q_v}(t)}$$

$q_a$ is a control parameter for accepting the probability P and $T_{q_v}$ is a temperature value.

As described herein, the probability P corresponds to a probability used in generalized simulated annealing methods, but in general, any suitable probability value may be used. At step 786, a random number r between 0 and 1, inclusive, is generated. The random number r may be generated from a uniform distribution, or any other suitable distribution, and r is compared to the probability P at decision block 788.

If P is greater than or equal to r, this means that the probability of accepting the second objective value is high, even though the second objective value was not smaller than the first objective value. In this case, the classifier 114 proceeds to step 790 and 792 to store the second vector X(2) and the second objective value as the first vector X(1) and the first objective value, respectively.

Alternatively, if at decision block 776, the classifier 114 determines that the second objective value is smaller than the first objective value, this means that the vector X(2) resulted in a better correlation, or better performance Thus, the classifier proceeds directly to step 790 to update the vector X(1) with the vector X(2), and to step 792 to update the first objective value with the second objective value. At step 794, the classifier 114 sets the count variable to be equal to 1.

Alternatively, if at decision block 788, the classifier 114 determines that r is greater than P, this means that the probability of accepting the second objective value is low, such that the steps 790 and 792 are bypassed, and the vector X(1) and first objective value are not overwritten by the corresponding second values. In this case, the classifier 114 proceeds to step 794 and sets the count variable to be equal to 1.

After re-setting the count variable to 1, the classifier 114 proceeds to decision block 796, where the iteration parameter y is compared to a value L. The value L corresponds to a maximal number of major perturbations to be performed before proceeding to the method depicted in FIG. 8 to perform minor perturbations. If the iteration parameter y is not equal to L, the classifier 114 proceeds to decision block 772 and step 774 to increment the iteration parameter y and perform a major perturbation of the vector X at steps 760-764. The steps described above are repeated until a desired number of major perturbations L have been performed. As depicted in FIG. 7, the number of major perturbations to be performed is a fixed number L. However, the value for L may be dependent on any number of factors. For example, the classifier 114 may determine that the total number of major perturbations has been reached based on a convergence of the objective values. In another example, the total number of major perturbations may be reached if no second objective values have been found to be less than the first objective value in a fixed number of recent comparisons at decision block 776. In general, any suitable method may be used to determine that the major perturbations are done, and that the classifier 114 may proceed to FIG. 8 to perform minor perturbations.

FIG. 8 is a flow diagram of a method for further decreasing an objective value in a binary generalized simulated annealing method by performing minor perturbations on the vector X. In particular, the method 800 begins at step 802 and sets a variable C equal to the length of the vector X(1). At step 804, the classifier 114 initializes an iteration parameter c to 1 and sets an improve flag variable to false.

At step 806, the classifier 114 performs a minor perturbation on the vector X(1) by flipping the $c^{th}$ bit of X(1) to generate $X_{temp}$. In particular, X(1) is a binary vector of length C, and $X_{temp}$ is nearly identical to X(1) except for the $c^{th}$ bit.

At step 808, the classifier 114 generates a result vector 810 and an objective value 812 for the temporary vector $X_{temp}$. In particular, the classifier 114 may use the method depicted in FIG. 5 to generate a temporary result vector and a temporary objective value. However, in general, any suitable method to determine an objective value representative of a composite performance metric may be used.

At decision block 814, the first objective value is compared to the temporary objective value. If the temporary objective value is smaller than the first objective value, this means that perturbed version $X_{temp}$ resulted in better performance than the original vector X(1). In this case, the classifier 114 proceeds to step 816 to overwrite the vector X(1) with the perturbed version $X_{temp}$, to step 818 to overwrite the first objective value with the temporary objective value, and to step 819 to set the improve flag variable to true.

At decision block 820, the classifier 114 determines whether each bit in the vector X(1) has been flipped at least once (i.e., at step 806), or equivalently, whether the iteration parameter c is equal to the size of X(1) C. If not, the classifier 114 proceeds to step 822 to increment the iteration parameter c and to step 806 to flip the $c^{th}$ bit.

Otherwise, if the classifier 114 determines that the iteration parameter c is equal to the length of the vector X(1) C at decision block 820, the classifier 114 proceeds to decision block 822 to determine whether further improvement is desired. In particular, the classifier 114 may identify the value of the improve flag variable to determine whether additional bit flipping is desirable. For example, if the improve flag variable is true, the classifier 114 returns to step 804 to re-initialize the iteration parameter c to 1 and the improve flag variable to false.

The depicted method in FIG. 8 uses the improve flag variable to determine when the process of performing minor perturbations (i.e., bit flipping) is complete. However, in general, any other suitable method may also be used to determine when the minor perturbations are complete. For example, the classifier 114 may require that the objective value is below some threshold, or that the difference between the objective value and the temporary objective value is below some threshold. If these requirements are not satisfied, the classifier 114 may return to step 806 to flip another bit of the vector X(1) to generate another temporary objective value.

After the classifier 114 has determined that the minimal objective value has been identified, the classifier 114 proceeds to steps 824 and 826 to increment the parameter t and decrement the parameter D, respectively.

At step 828, the classifier 114 computes a temperature T by the cooling formula commonly used in generalized simulated annealing. However, any suitable formula may be used.

$$T_{q_v}(t) \leftarrow T_{q_v}(1)\frac{2^{q_v-1}-1}{(1+t)^{q_v-1}-1}$$

where $q_v$ is a parameter defining the curvature of the distribution function.

At decision block 830, the classifier 114 determines whether $T_{q_v}(t)$ is less than $T_L$. The value for $T_L$ represents a threshold value, where if the value for $T_{q_v}(t)$ is below $T_L$, the method 800 ends, and the current random vector X(1) is used as the optimal classification.

Implementations of the present subject matter can include, but are not limited to, systems methods and computer program products comprising one or more features as described herein as well as articles that comprise a machine-readable medium operable to cause one or more machines (e.g., computers, robots) to result in operations described herein. The methods described herein can be implemented by one or more processors or engines residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems.

Figure 9:
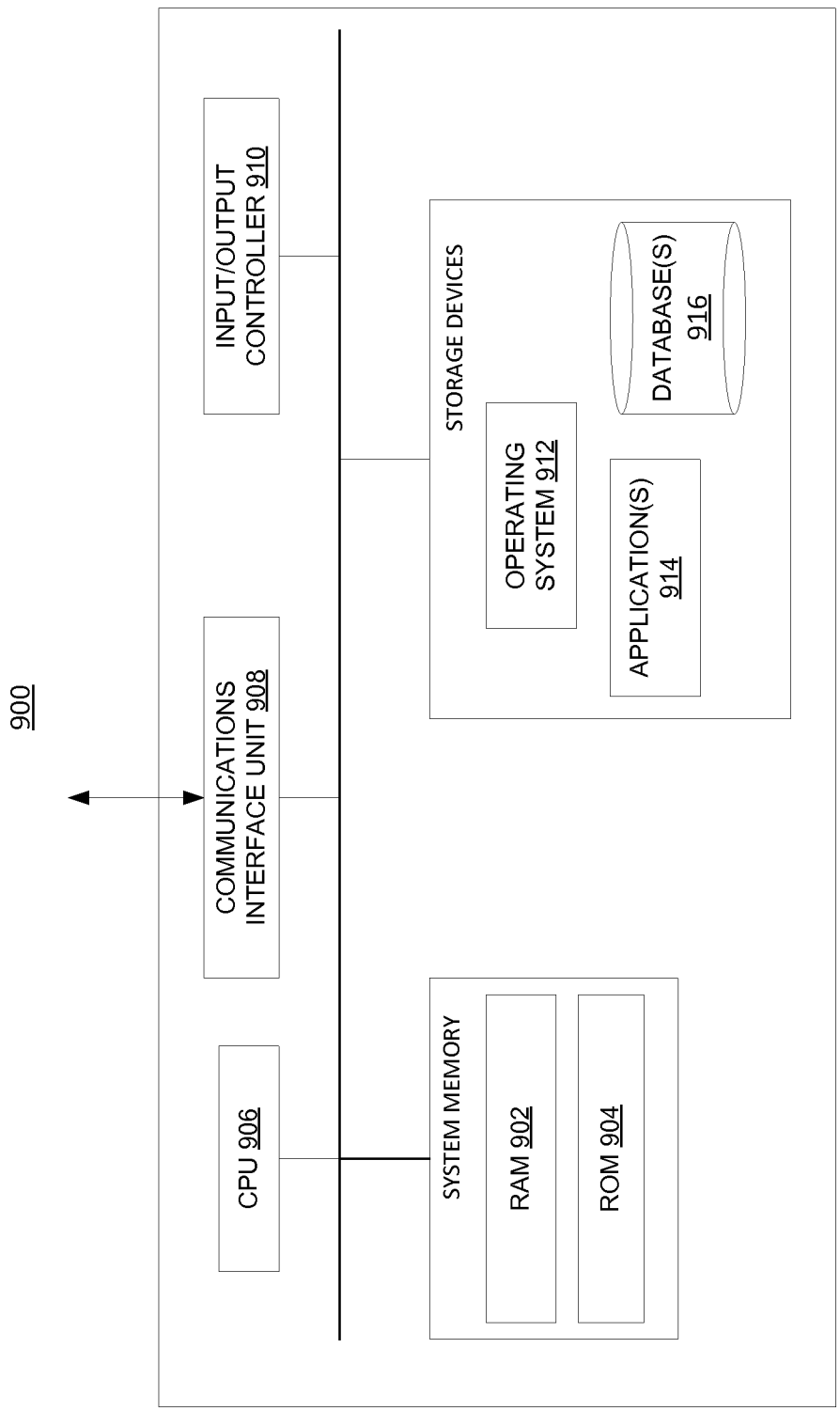
FIG. 9 is a block diagram of a computing device, such as any of the components of the system of FIG. 1.

FIG. 9 is a block diagram of a computing device, such as any of the components of system 100 of FIG. 1 including circuitry for performing processes described with reference to FIGS. 2-8. Each of the components of system 100 may be implemented on one or more computing devices 900. In certain aspects, a plurality of the above-components and databases may be included within one computing device 900. In certain implementations, a component and a database may be implemented across several computing devices 900.

The computing device 900 comprises at least one communications interface unit, an input/output controller 910, system memory, and one or more data storage devices. The system memory includes at least one random access memory (RAM 902) and at least one read-only memory (ROM 904). All of these elements are in communication with a central processing unit (CPU 906) to facilitate the operation of the computing device 900. The computing device 900 may be configured in many different ways. For example, the computing device 900 may be a conventional standalone computer or alternatively, the functions of computing device 900 may be distributed across multiple computer systems and architectures. The computing device 900 may be configured to perform some or all of data-splitting, differentiating, classifying, scoring, ranking and storing operations. In FIG. 9, the computing device 900 is linked, via network or local network, to other servers or systems.

The computing device 900 may be configured in a distributed architecture, wherein databases and processors are housed in separate units or locations. Some such units perform primary processing functions and contain at a minimum a general controller or a processor and a system memory. In such an aspect, each of these units is attached via the communications interface unit 908 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 906 comprises a processor, such as one or more conventional microprocessors and one or more supplementary co-processors such as math co-processors for offloading workload from the CPU 906. The CPU 906 is in communication with the communications interface unit 1008 and the input/output controller 910, through which the CPU 906 communicates with other devices such as other servers, user terminals, or devices. The communications interface unit 908 and the input/output controller 910 may include multiple communication channels for simultaneous communication with, for example, other processors, servers or client terminals. Devices in communication with each other need not be continually transmitting to each other. On the contrary, such devices need only transmit to each other as necessary, may actually refrain from exchanging data most of the time, and may require several steps to be performed to establish a communication link between the devices.

The CPU 906 is also in communication with the data storage device. The data storage device may comprise an appropriate combination of magnetic, optical or semiconductor memory, and may include, for example, RAM 902, ROM 904, flash drive, an optical disc such as a compact disc or a hard disk or drive. The CPU 906 and the data storage device each may be, for example, located entirely within a single computer or other computing device; or connected to each other by a communication medium, such as a USB port, serial port cable, a coaxial cable, an Ethernet type cable, a telephone line, a radio frequency transceiver or other similar wireless or wired medium or combination of the foregoing. For example, the CPU 906 may be connected to the data storage device via the communications interface unit 908. The CPU 906 may be configured to perform one or more particular processing functions.

The data storage device may store, for example, (i) an operating system 1012 for the computing device 900; (ii) one or more applications 914 (e.g., computer program code or a computer program product) adapted to direct the CPU 906 in accordance with the systems and methods described here, and particularly in accordance with the processes described in detail with regard to the CPU 906; or (iii) database(s) 916 adapted to store information that may be utilized to store information required by the program. In some aspects, the database(s) includes a database storing experimental data, and published literature models.

The operating system 912 and applications 914 may be stored, for example, in a compressed, an uncompiled and an encrypted format, and may include computer program code. The instructions of the program may be read into a main memory of the processor from a computer-readable medium other than the data storage device, such as from the ROM 904 or from the RAM 902. While execution of sequences of instructions in the program causes the CPU 906 to perform the process steps described herein, hard-wired circuitry may be used in place of, or in combination with, software instructions for implementation of the processes of the present invention. Thus, the systems and methods described are not limited to any specific combination of hardware and software.

Suitable computer program code may be provided for performing one or more functions in relation to performing classification methods as described herein. The program also may include program elements such as an operating system 912, a database management system and "device drivers" that allow the processor to interface with computer peripheral devices (e.g., a video display, a keyboard, a computer mouse, etc.) via the input/output controller 910.

A computer program product comprising computer-readable instructions is also provided. The computer-readable instructions, when loaded and executed on a computer system, cause the computer system to operate according to the method, or one or more steps of the method described above. The term "computer-readable medium" as used herein refers to any non-transitory medium that provides or participates in providing instructions to the processor of the computing device 900 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 906 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 900 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

EXAMPLE

The following public datasets are downloaded from the Gene Expression Omnibus (GEO) (http://www.ncbi.nlm.nih.gov/geo/) repository:
- a. GSE10106 (www.ncbi.nlm.nih.gov/geo/query/acc.cgi?acc=GSE10106)
- b. GSE10135 (www.ncbi.nlm.nih.gov/geo/query/acc.cgi?acc=GSE10135)
- c. GSE11906 (www.ncbi.nlm.nih.gov/geo/query/acc.cgi?acc=GSE11906)
- d. GSE11952 (www.ncbi.nlm.nih.gov/geo/query/acc.cgi?acc=GSE11952)
- e. GSE13933 (www.ncbi.nlm.nih.gov/geo/query/acc.cgi?acc=GSE13933)
- f. GSE19407 (www.ncbi.nlm.nih.gov/geo/query/acc.cgi?acc=GSE19407)
- g. GSE19667 (www.ncbi.nlm.nih.gov/geo/query/acc.cgi?acc=GSE19667)
- h. GSE20257 (www.ncbi.nlm.nih.gov/geo/query/acc.cgi?acc=GSE20257)
- i. GSE5058 (www.ncbi.nlm.nih.gov/geo/query/acc.cgi?acc=GSE5058)
- j. GSE7832 (www.ncbi.nlm.nih.gov/geo/query/acc.cgi?acc=GSE7832)
- k. GSE8545 (www.ncbi.nlm.nih.gov/geo/query/acc.cgi?acc=GSE8545).

Figure 10:
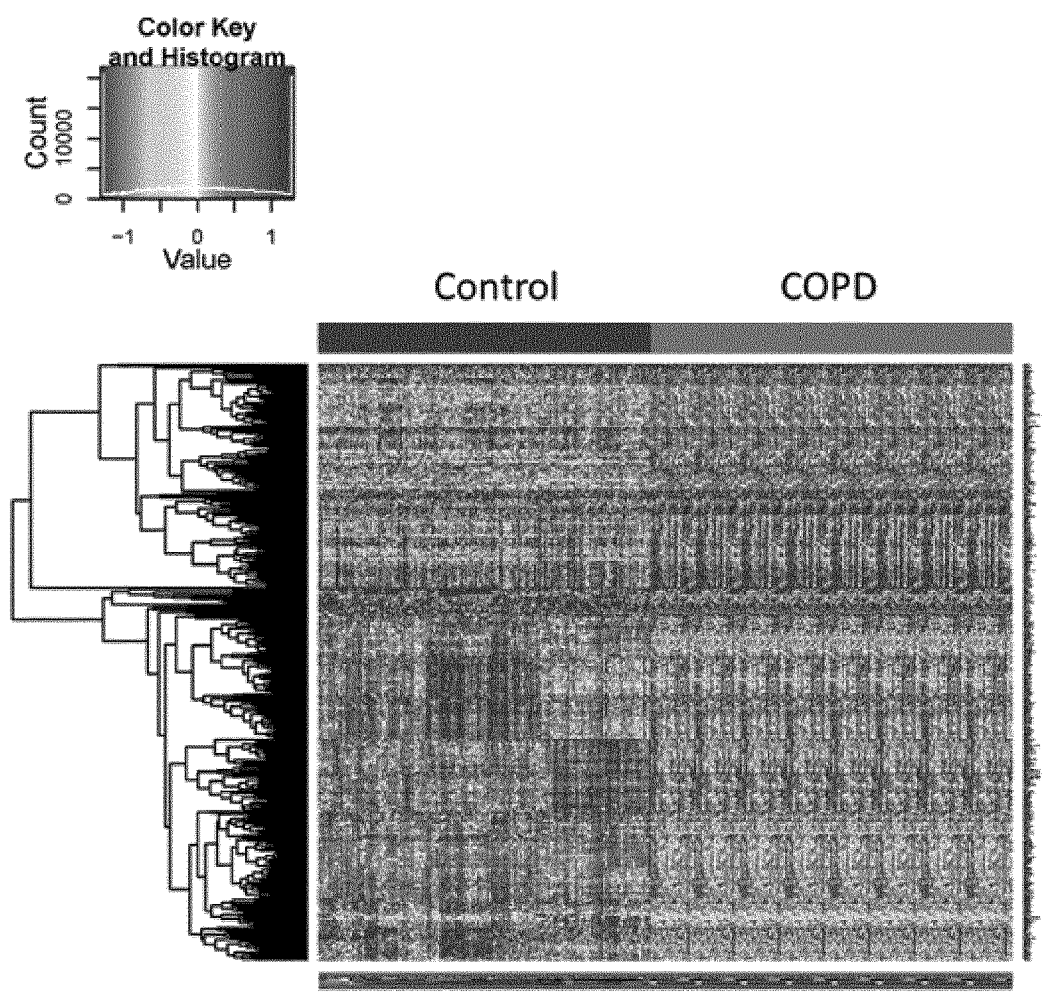
FIG. 10 is a heatmap of a gene signature in a training data set.

The training datasets are on the Affymetrix platform (HGU-133+2). Raw data files are read by the ReadAffy function of the affy package (Gautier, 2004) belonging to Bioconductor (Gentleman, 2004) in R (R Development Core Team, 2007), and the quality is controlled by: generating RNA degradation plots (with the AffyRNAdeg function of the affy package), NUSE and RLE plots (with the function affyPLM (Brettschneider, 2008)), and calculating the MA(RLE) values; excluding arrays from the training datasets that fell below a set of thresholds on the quality control checks or that are duplicated in the above datasets; and normalizing arrays that pass quality control checks using the gcrma algorithm (Wu, 2004). Training set sample classifications are obtained from the series matrix file of the GEO database for each dataset. The output consists of a gene expression matrix with 54675 probesets for 233 samples (28 COPD samples and 205 control sample). To make a balanced data set, the COPD samples were multiple time to obtain 224 COPD samples before the Duel Ensemble method as described in copending U.S. provisional application 61/662,812 is applied. With a combined data set which contains 205 control and 224 COPD patients, a gene signature with 409 genes was built. 850 binary values were used in the random vectors. The classification methods used in the method included the following R packages: lda, svm, randomForest, knn, pls.lda and pamr. Maximum iteration was set to be 5000. The Matthew's Correlation Coefficient (MCC) and accuracy in cross validation process in training data set is 0.743 and 0.87 respectively. The heatmap of the gene signature in training data set is shown in FIG. 10. In the heatmap of FIG. 10, the gene expression value was centered by row. The colors of the heatmap may not be clearly shown in grey scale, but the data of FIG. 10 show that control data are shown on the left, and COPD data are shown on the right. The test data set is an unpublished data set obtained from a commercial supplier (Genelogic), which contains 16 control samples and 24 COPD samples. Without applying the transformation invariant method of the invention, the gene signature generated by Dual Ensemble correctly predicted 29 samples out of total 40 samples. The accuracy is 0.725, and the MCC is 0.527. The gene signature correctly predicted 15 out of 16 control samples and correctly predicted 14 out of 24 COPD samples.

While implementations of the invention have been particularly shown and described with reference to specific examples, it should be understood by those skilled in the art that various changes in form and detail may be made therein without departing from the spirit and scope of the disclosure.

The invention claimed is:

1. A computer-implemented method of classifying a data set into two or more classes executed by a processor, comprising:
   (a) receiving a training data set associated with the data set and having a set of known labels, wherein the data set comprises gene set data, and each gene set data corresponds to one of a plurality of biological state classes, and wherein the labels identify the biological state classes of the gene set data;
   (b) generating a first classifier for the training data set by applying a first machine learning technique to the training data set, wherein the first machine learning technique identifies a first set of classification methods, wherein each classification method votes on the training data set;
   (c) classifying elements in the training data set according to the first classifier to obtain a first set of predicted labels for the training data set;
   (d) computing a first objective value from the first set of predicted labels and the set of known labels;
   (e) for each of a plurality of iterations, performing the following steps (i)-(v):
      (i) generating a second classifier for the training data set by applying a second machine learning technique to the training data set, wherein the second machine learning technique identifies a second set of classification methods that is different from the first set of classification methods by at least one classification method, wherein each classification method votes on the training data set;
      ii) classifying the elements in the training data set according to the second classifier to obtain a second set of predicted labels for the training data set;
      (iii) computing a second objective value from the second set of predicted labels and the set of known labels;
      (iv) comparing the first objective value to the second objective value to determine whether the second classifier outperforms the first classifier; and
      (v) replacing the first set of predicted labels with the second set of predicted labels and replacing the first objective value with the second objective value when the second classifier outperforms the first classifier, and return to step (i); and
   (f) when a desired number of iterations has been reached, outputting the first set of predicted labels.

2. The method of claim 1, wherein the training data set is formed by selecting a subset of training data samples from an aggregate training data set, the method further comprising bootstrapping the aggregate training data set to generate a plurality of additional training data sets, and repeating the steps (a) through (f) for each additional training data set.

3. The method of claim 2, wherein the bootstrapping is performed with balanced samples.

4. The method of claim 1, further comprising:
   selecting a sample in a test data set that is different from the training data set and does not have a set of known labels; and
   using the identified classifier to predict a label for the selected sample.

5. The method of claim 1, wherein:
   the first set of classification methods is obtained by using a first random vector to select a subset of an aggregate set of classification methods;
   the first random vector includes a set of binary values corresponding to the aggregate set of classification methods;
   each binary value indicates whether the corresponding classification method in the aggregate set is included in the first set of classification methods; and
   the second set of classification methods is obtained by using a second random vector including a different set of binary values.

6. The method of claim 5, wherein the first random vector includes parameters include a flag variable indicating whether to perform balanced bootstrapping, a number of bootstraps, a list of classification methods, a list of genes, or a combination thereof.

7. The method of claim 5, wherein the step of computing the second objective value comprises implementing a simulated annealing method.

8. The method of claim 7, wherein the simulated annealing method comprises updating one or more values of the first random vector to obtain the second random vector.

9. The method of claim 8, wherein:
   updating the one or more values of the first random vector comprises randomly updating each element of the first random vector to obtain the second random vector.

10. The method of claim 5, wherein:
    the plurality of iterations includes a first set of iterations and a second set of iterations; and each subsequent second random vector differs from a previous second random vector by an amount that is larger for the first set of iterations than for the second set of iterations.

11. The method of claim 10, wherein for each iteration in the first set of iterations and in the second set of iterations,
    a first subset of the subsequent second random vector is selected to be the same as a corresponding first subset of the previous second random vector,
    a second subset of the subsequent second random vector is selected to be different from a corresponding second subset of the previous second random vector,
    a size of the first subset is smaller for the first set of iterations than for the second set of iterations, and
    a size of the second subset is larger for the first set of iterations than for the second set of iterations.

12. The method of claim 11, wherein the size of the second subset for the first set of iterations is approximately 20% of the length of the second random vector, and the size of the second subset for the second set of iterations is one.

13. The method of claim 1, wherein the second objective value corresponds to a Matthew correlation coefficient that is assessed from the second set of predicted labels and the set of known labels.

14. The method of claim 1, further comprising:
    determining that the second classifier outperforms than the first classifier when the second objective value is less than the first objective value, and if the second objective value is greater than the first objective value, when a random value is less than a probability value that is computed from the first objective value and the second objective value.

15. The method of claim 14, wherein the probability value is computed from a control parameter q, the first objective value, the second objective value, and a temperature value that is computed from a cooling formula.

16. The method of claim 1, wherein the second classifier is selected from a group comprising linear discriminant analysis, support vector machine-based methods, random forest methods, and k nearest neighbor methods.

17. The method of claim 1, wherein the biological state classes indicate diseased or diseased-free.

18. The method of claim 1, wherein the elements in the training data set are classified using a classification rule associated with the first classifier to obtain the first set of predicted labels for the training data set, and the elements in the training data set are classified using a classification rule associated with the second classifier to obtain the second set of predicted labels for the training data set.

19. A computer program product comprising computer-readable instructions that, when executed in a computerized system comprising at least one processor, cause the processor to carry out a method, comprising:
    (a) receiving a training data set associated with a data set and having a set of known labels, wherein the data set comprises gene set data, and each gene set data corresponds to one of a plurality of biological state classes, and wherein the labels identify the biological state classes of the gene set data;
    (b) generating a first classifier for the training data set by applying a first machine learning technique to the training data set, wherein the first machine learning technique identifies a first set of classification methods, wherein each classification method votes on the training data set;
    (c) classifying elements in the training data set according to the first classifier to obtain a first set of predicted labels for the training data set;
    (d) computing a first objective value from the first set of predicted labels and the set of known labels;
    (e) for each of a plurality of iterations, performing the following steps (i)-(v):
        (i) generating a second classifier for the training data set by applying a second machine learning technique to the training data set, wherein the second machine learning technique identifies a second set of classification methods that is different from the first set of classification methods by at least one classification method, wherein each classification method votes on the training data set;
        (ii) classifying the elements in the training data set according to the second classifier to obtain a second set of predicted labels for the training data set;
        (iii) computing a second objective value from the second set of predicted labels and the set of known labels
        (iv) comparing the first objective value to the second objective value to determine whether the second classifier outperforms the first classifier; and
        (v) replacing the first set of predicted labels with the second set of predicted labels and replacing the first objective value with the second objective value when the second classifier outperforms the first classifier, and return to step (i); and
    (f) when a desired number of iterations has been reached, outputting the first set of predicted labels.

20. A computerized system comprising a processing device configured with non-transitory computer-readable instructions that, when executed, cause the processing device to carry out a method comprising:
    (a) receiving a training data set associated with a data set and having a set of known labels, wherein the data set comprises gene set data, and each gene set data corresponds to one of a plurality of biological state classes, and wherein the labels identify the biological state classes of the gene set data;
    (b) generating a first classifier for the training data set by applying a first machine learning technique to the training data set, wherein the first machine learning technique identifies a first set of classification methods, wherein each classification method votes on the training data set;
    (c) classifying elements in the training data set according to the first classifier to obtain a first set of predicted labels for the training data set;
    (d) computing a first objective value from the first set of predicted labels and the set of known labels;
    (e) for each of a plurality of iterations, performing the following steps (i)-(v):
        (i) generating a second classifier for the training data set by applying a second machine learning technique to the training data set, wherein the second machine learning technique identifies a second set of classification methods that is different from the first set of classification methods by at least one classification method, wherein each classification method votes on the training data set;
        (ii) classifying the elements in the training data set according to the second classifier to obtain a second set of predicted labels for the training data set;
        (iii) computing a second objective value from the second set of predicted labels and the set of known labels;
        (iv) comparing the first objective value to the second objective value to determine whether the second classifier outperforms the first classifier;
        (v) replacing the first set of predicted labels with the second set of predicted labels and replacing the first objective value with the second objective value when the second classifier outperforms the first classifier, and return to step (i); and
    (f) when a desired number of iterations has been reached, outputting the first set of predicted labels.

* * * * *